(12) United States Patent
Li

(10) Patent No.: US 10,709,771 B2
(45) Date of Patent: Jul. 14, 2020

(54) METHOD FOR PREVENTING OR TREATING DIABETIC RETINOPATHY

(71) Applicant: TALENGEN INTERNATIONAL LIMITED, Hong Kong (CN)

(72) Inventor: Jinan Li, Shenzhen (CN)

(73) Assignee: TALENGEN INTERNATIONAL LIMITED, Hong Kong (CN)

( * ) Notice: Subject to any disclaimer, the term of this patent is extended or adjusted under 35 U.S.C. 154(b) by 4 days.

(21) Appl. No.: 16/062,052

(22) PCT Filed: Dec. 16, 2016

(86) PCT No.: PCT/CN2016/110452
§ 371 (c)(1),
(2) Date: Jun. 13, 2018

(87) PCT Pub. No.: WO2017/101870
PCT Pub. Date: Jun. 22, 2017

(65) Prior Publication Data
US 2018/0360930 A1    Dec. 20, 2018

(30) Foreign Application Priority Data
Dec. 18, 2015    (WO) ................ PCT/CN2015/097946

(51) Int. Cl.
| A61K 38/00 | (2006.01) |
| A61K 38/48 | (2006.01) |
| A61P 27/02 | (2006.01) |
| A61P 3/10 | (2006.01) |
| A61K 45/06 | (2006.01) |

(52) U.S. Cl.
CPC ............ *A61K 38/484* (2013.01); *A61K 38/48* (2013.01); *A61K 45/06* (2013.01); *A61P 3/10* (2018.01); *A61P 27/02* (2018.01); *C12Y 304/21007* (2013.01)

(58) Field of Classification Search
None
See application file for complete search history.

(56) References Cited

U.S. PATENT DOCUMENTS

| 2003/0113313 A1* | 6/2003 | Peyman .................. A61F 2/147 424/94.63 |
| 2003/0147876 A1 | 8/2003 | Ni |
| 2003/0180934 A1 | 9/2003 | Ni et al. |
| 2005/0250694 A1 | 11/2005 | Ma |
| 2007/0196350 A1 | 8/2007 | Bartels |
| 2013/0273028 A1 | 10/2013 | Zwaal |
| 2018/0369345 A1 | 12/2018 | Li |
| 2019/0015485 A1 | 1/2019 | Li |

FOREIGN PATENT DOCUMENTS

| CA | 2703494 A1 | 4/2009 |
| CN | 1451746 A | 10/2003 |
| CN | 1585649 A | 2/2005 |
| CN | 1643140 A | 7/2005 |
| CN | 1768138 A | 5/2006 |
| CN | 1946352 A | 4/2007 |
| CN | 1961958 A | 5/2007 |
| CN | 1990871 A | 7/2007 |
| CN | 101002888 A | 7/2007 |
| CN | 101563100 A | 10/2009 |
| CN | 101573134 A | 11/2009 |
| CN | 101918548 A | 12/2010 |
| CN | 102121023 A | 7/2011 |
| CN | 102154253 A | 8/2011 |
| CN | 102250210 A | 11/2011 |
| CN | 102872020 A | 1/2013 |
| CN | 103384722 A | 11/2013 |
| CN | 103764163 A | 4/2014 |
| CN | 104789544 A | 7/2015 |
| CN | 105008323 A | 10/2015 |
| CN | 105705520 A | 6/2016 |
| JP | 2009-196927 A | 9/2009 |
| JP | 2019500422 A | 1/2019 |
| TW | 201625294 A | 7/2016 |
| TW | 201822800 A | 7/2018 |
| TW | 201822801 A | 7/2018 |
| TW | 201822802 A | 7/2018 |
| TW | 201822803 A | 7/2018 |
| TW | 201822804 A | 7/2018 |
| TW | 201822807 A | 7/2018 |
| TW | 201822808 A | 7/2018 |
| WO | WO199900420 A1 | 1/1999 |
| WO | WO200018436 A1 | 4/2000 |
| WO | WO-2003/020297 A2 | 3/2003 |
| WO | WO-2003/020297 A3 | 3/2003 |
| WO | WO2003066842 A2 | 8/2003 |
| WO | WO2003095637 A1 | 11/2003 |
| WO | WO2003066842 A3 | 6/2004 |
| WO | WO2004052228 A2 | 6/2004 |

(Continued)

OTHER PUBLICATIONS

Gao Get al.Diabetes, 51: 1218-1225,2002.*
Ajjan, R.A. et al. (Jul. 4, 2013)."Diabetes Is Associated With Posttranslational Modifications in Plasminogen Resulting in Reduced Plasmin Generation and Enzyme-Specific Activity." *Blood* 122(1):134-142.
Andreasen, P.A. et al. (1997). "The Urokinase-Type Plasminogen Activator System in Cancer Metastasis: A Review," *Int. J. Cancer* 72:1-22.
Chen, W. (Apr. 15, 2007). "Pilot Production and Pharmacodynamics Study of Recombinant Human Microplasminogen," Doctoral Dissertation, Fudan University, 127 pages. (With English Abstract).
Collen, D. et al. (Dec. 15, 1991) "Review Article: Basic and Clinical Aspects of Fibrinolysis and Thrombolysis," *Blood* 78(12):3114-3124.

(Continued)

*Primary Examiner* — Jeanette M Lieb
(74) *Attorney, Agent, or Firm* — Morrison & Foerster LLP

(57) ABSTRACT

The present invention relates to the effect of plasminogen in the prevention or treatment of retinopathy caused by diabetes mellitus, thereby providing a new therapeutic strategy for treating different types of diabetes mellitus-related retinopathy.

8 Claims, 9 Drawing Sheets

Specification includes a Sequence Listing.

(56) References Cited

FOREIGN PATENT DOCUMENTS

| | | | |
|---|---|---|---|
| WO | WO2004052228 A3 | 10/2004 | |
| WO | WO-2008/026999 A2 | 3/2008 | |
| WO | WO-2008/026999 A3 | 3/2008 | |
| WO | WO2009073471 A1 | 6/2009 | |
| WO | WO2012093132 A1 | 7/2012 | |
| WO | WO2013024074 A1 | 2/2013 | |
| WO | WO2014070983 A1 | 5/2014 | |
| WO | WO2014070986 A1 | 5/2014 | |
| WO | WO2015023752 A1 | 2/2015 | |
| WO | WO2016095013 A1 | 6/2016 | |
| WO | WO2017101866 A1 | 6/2017 | |
| WO | WO2017101868 A1 | 6/2017 | |

OTHER PUBLICATIONS

Collen, D. (2001). "Ham-Wasserman Lecture: Role of the Plasminogen System in Fibrin-Homeostasis and Tissue Remodeling," *Hematology* pp. 1-9.

Davalos, D. et al. (2012, e-pub. Oct. 31, 2011). "Fibrinogen as a Key Regulator of Inflammation in Disease," *Semin. Immunopathol.* 34:43-62.

Du, Z. et al. (Dec. 31, 1997). "Changes of Plasm tPA and PAI Activities in Patients With Diabetic Retinopathy," *Eye Science* 13(1):17-20.

Gao, C. et al. (Feb. 2007). "Relationship Between Type Diabetic Retinopathy and Plasma Fibrinolysis," *Progress in Modern Biomedicine* 7(2):257-258. (With English Abstract).

Hay, E.D. (1991). Cell Biology of Extracellular Matrix, 2$^{nd}$ Ed. Springer Science+Business Media, LLC., 15 pages. Table of Contents.

He, C. et al. (Apr. 1989). "Tissue Cooperation in a Proteolytic Cascade Activating Human Interstitial Collagenase," *Proc. Natl. Acad. Sci. USA* 86:2632-2636.

Hunt, J.A. et al. (2008, e-pub. Aug. 14, 2008). "Simplified Recombinant Plasmin: Production and Functional Comparison of a Novel Thrombolytic Molecule With Plasma-Derived Plasmin," *Thromb. Haemost.* 100:413-419.

Jin, X. et al. (Aug. 2002). "Catabolic Enzymes of Extracellular Matrix and Diabetic Nephropathy," *Medical Journal of the Chinese Coal Industry* 5(8):825-826. With English Translation.

Knudsen, B.S. et al. (Aug. 15, 1986). "Binding of Plasminogen to Extracellular Matrix," *The Journal of Biological Chemistry* 261(23):10765-10771.

Lee, H.B. et al. (2005). "Plasminogen Activator Inhibitor-1 and Diabetic Nephropathy," *Nephrology* 10:S11-S13.

Li, J. et al. (Sep. 2008). "Catabolic Enzymes of Extracellular Matrix and Diatetic Nephropathy," *Medical Recapitulate* 14(17):2611-2613. (English Translation Abstract Only).

Marder, V. J. et al. (2010). "Direct Fibrinolytic Agents: Biochemical Attributes, Preclinical Foundation and Clinical Potential," *J. Thromb. Haemost.* 8:433-444.

Mignatti, P. et al. (Jan. 1993). "Biology and Biochemistry of Proteinases in Tumor Invasion," *Physiological Reviews* 73(1):161-195.

Nagai, N. et al. (2002). "Recombinant Human Microplasmin: Production and Potential Therapeutic Properties," *Journal of Thrombosis and Haemostasis* 1:307-313.

Raum, D. et al. (May 30, 1980). "Synthesis of Human Plasminogen by the Liver," *Science* 208(4447):1036-1037, 4 pages.

Rifkin, D.B. et al. (1990). "Growth Factor Control of Extracellular Proteolysis," *Cell Differentiation and Development* 32:313-318.

Rifkin, D.B. et al. (1999). "Proteolytic Control of Growth Factor Availability," *APMIS* 107:80-85.

Ryu, J.K. et al. (Sep. 10, 2015). "Blood Coagulation Protein Fibrinogen Promotes Autoimmunity and Demyelination via Chemokine Release and Antigen Presentation," *Nature Communication* 6:8164, 15 pages.

Saksela, O. et al. (1988). "Cell-Associated Plasminogen Activation: Regulation and Physiological Functions," *Ann. Rev. Cell Biol.* 4:93-126.

Shen, Y. et al. (Jun. 14, 2012). "Plasminogen Is a Key Proinflammatory Regulator That Accelerates the Healing of Acute and Diabetic Wounds," *Blood* 119(24):5879-5887.

Shi, L. et al. (Nov. 30, 2005). "Comparison of Curative Effects of Kallidinogenase Between Patients with Early Diabetic Nephropathy and Patients with Clinical Diabetic Nephropathy," *Journal of Jilin University (Medicine Edition)*, 31(6):934-936. (With English Abstract).

Singh, R. et al. (Dec. 21, 2014). "Diabetic Peripheral Neuropathy: Current Perspective and Future Directions," *Pharmacological Research* 80:21-35.

Sottrup-Jensen, L. et al. (Jul. 1975). "Amino-acid Sequence of Activation Cleavage Site in Plasminogen: Homology With 'Pro' Part of Prothrombin," *Proc. Natl. Acad. Sci. USA* 72(7):2577-2581.

Stoppelli, M.P. et al. (Aug. 1985). "Differentiation-enhanced Binding of the Amino-Terminal Fragment of Human Urokinase Plasminogen Activator to a Specific Receptor on U937 Monocytes," *Proc. Natl. Acad. Sci. USA* 82:4939-4973.

Tyagi, S.C. (1997). "Proteinases and Myocardial Extracellular Matrix Turnover," *Molecular and Cellular Biochemistry* 168:1-12.

Valvi, D. et al. (Mar. 6, 2012). "Fibrinogen, Chronic Obstructive Pulmonary Disease (COPD) and Outcomes in Two United States Cohorts," *International Journal of COPD* 7:173-182.

Vassalli, J.-D. et al. (Jan. 1985). "A Cellular Binding Site for the $M_r$-55,000 Form of the Human Plasminogen Activator, Urokinase," *The Journal of Cell Biology* 100:86-92.

Wang, X. (Mar. 31, 2014). "Medical Treatment of Painful Diabetic Neuropathy," *Journal of Community Medicine* 12(6):82 & 83, with English Translation Abstract.

Werb, Z. et al. (May 5, 1977). "Endogenous Activation of Latent Collagenase by Rheumatoid Synovial Cells," *The New England Journal of Medicine* 296(18):1017-1023.

Wiman, B. et al. (1975). "Structural Relationship between 'Glutamic Acid' and 'Lysine' Forms of Human Plasminogen and Their Interaction with the $NH_2$-Terminal Activation Peptide as Studied by Affinity Chromatography," *Eur. J. Biochem* 50:489-494.

Xu, A. et al. (Feb. 28, 2014). "New Progress in the Treatment of Diabetic Neuropathic Pain," *Chinese Journal of Clinical Research* 27(2):227,228 & 230, with English Translation Abstract.

Yin, G. et al. (2005) "Cloning Construction and Purification of Recombinant Human Plasminogen Kringle 5 Gene," *Academic Journal of Shanghai Second Medical University* 25(2):151-154. (English Translation of the Abstract).

International Search Report, dated Mar. 21, 2017, for PCT Application No. PCT/CN2016/110449, filed Dec. 16, 2016, 6 pages.

International Search Report, dated Mar. 2, 2017, for PCT Application No. PCT/CN2016/110450, filed Dec. 16, 2016, 4 pages.

International Search Report, dated Feb. 24, 2017, for PCT Application No. PCT/CN2016/110452, filed Dec. 16, 2016, 4 pages.

U.S. Appl. No. 16/063,569, Li, J., filed Jun. 18, 2018, (Copy not submitted herewith pursuant to the waiver of 37 C.F.R. § 1.98(a)(2)(iii) issued by the Office on Sep. 21, 2004).

U.S. Appl. No. 16/063,534, Li, J., filed Jun. 18, 2018, (Copy not submitted herewith pursuant to the waiver of 37 C.F.R. § 1.98(a)(2)(iii) issued by the Office on Sep. 21, 2004).

U.S. Appl. No. 16/062,410, Li, J., filed Jun. 14, 2018. (Copy not submitted herewith pursuant to the waiver of 37 C.F.R. § 1.98(a)(2)(iii) issued by the Office on Sep. 21, 2004).

U.S. Appl. No. 16/062,421, Li, J., filed Jun. 14, 2018. (Copy not submitted herewith pursuant to the waiver of 37 C.F.R. § 1.98(a)(2)(iii) issued by the Office on Sep. 21, 2004).

U.S. Appl. No. 16/062,389, Li, J., filed Jun. 14, 2018. (Copy not submitted herewith pursuant to the waiver of 37 C.F.R. § 1.98(a)(2)(iii) issued by the Office on Sep. 21, 2004).

U.S. Appl. No. 16/062,037, Li, J., filed Jun. 13, 2018. (Copy not submitted herewith pursuant to the waiver of 37 C.F.R. § 1.98(a)(2)(iii) issued by the Office on Sep. 21, 2004).

U.S. Appl. No. 16/062,049, Li, J., filed Jun. 13, 2018. (Copy not submitted herwith pursuant to the waiver of 37 C.F.R. § 1.98(a)(2)(iii) issued by the Office on Sep. 21, 2004).

(56) References Cited

OTHER PUBLICATIONS

Aisina, R.B. et al. (2014). "Structure and Function of Plasminogen/Plasmin System," Russian Journal of Bioorganic Chemistry 40(6):590-605.
Akassoglou, K. et al. (May 29, 2000). "Tissue Plasminogen Activator—Mediated Fibrinolysis Protects Against Axonal Degeneration and Demyelination after Sciatic Nerve Injury," J Cell Biol. 149(5):1157-1166.
Auwerx, J. et al. (Jan./Feb. 1988). "Tissue-Type Plasminogen Activator Antigen and Plasminogen Activator Inhibitor in Diabetes Mellitus," Arteriosclerosis 8(1):68-72.
Bhattacharya, R. et al. (Mar. 15, 2017). "Impact of Genetic Variations on Three Dimensional Structure and Function of Proteins," PLoS ONE 12(3):e0171355, retrieved from https://doi.org/10.1371/journal.pone.0171355, 22 pages.
Brazionis, L. et al. (Apr. 2008). "Plasminogen Activator Inhibitor-1 Activity in Type 2 Diabetes a Different Relationship With Coronary Heart Disease and Diabetic Retinopathy," Arterioscler Thromb Vasc. Biol. 28:786-791.
Fisher, E.J. et al. (1997). "Displacement of Tissue Bound Plasminogen by Glucose: A Possible Mechanism in the Pathogenesis of Diabetic Nephropathy," Endocrinology and Metabolism 4:371-376, 8 pages.
Fowler, M.J. (2008). "Microvascular and Macrovascular Complications of Diabetes," Clinical Diabetes 26(2):77-82.
Gutiérrez-Fernández, A. et al. (Oct. 7, 2009). "Plasminogen Enhances Neuritogenesis on Laminin-1," J Neurosci. 29(40):12393-12400, 17 pages.
Hafer-Macko, C.E. et al. (Jul. 17, 2007). "Microvascular Tissue Plasminogen Activator Is Reduced in Diabetic Neuropathy," Neurology 69(3):268-274.
Kimiyoshi, A. (2009). "Diabetes and Peripheral Neuropathy," Forefront of Medicine and Medical Care 98 (2):399-405, 20 pages. English Translation.
Lugea, A. et al. (Sep. 2006). "Pancreas Recovery Following Caerulein-Induced Pancreatitis is Impaired in Plasminogen Deficient Mice," Gastroenterology 131(3):885-899, 32 pages.
Ma, L.-J. et al. (Feb. 2004). "Prevention of Obesity and Insulin Resistance in Mice Lacking Plasminogen Activator Inhibitor 1," Diabetes 53:336-346.
Ma, Q. et al. (Nov. 13, 2014, e-pub. Sep. 10, 2014). "Genetic Variants in PLG, LPA, and SIGLEC 14 as Nell as Smoking Contribute to Plasma Plasminogen Levels," Blood 124:3155-3164.
Martin-Fernandez et al. (Dec. 15, 2016). "The Unravelling of the Genetic Architecture of Plasminogen Deficiency and its Relation to Thrombotic Disease," Scientific Reports 6:39255, 7 pages.
Miles, L.A. et al. (Nov. 11, 2016). "Abstract 19088 the Plasminogen Receptor, Plg-Rkt, Regulates Metabolic Homeostasis and Promotes Healthy Adipose Function," Circulation 134(Suppl 1), 2 pages.
Mirsky, I.A. et al. (1958). "The Destruction of Glucagon, Adrenocorticotropin and Somatotropin by Human Blood Plasma," J. Clin. Invest. 28:14-20.
NCBI Reference Sequence—NP_000292.1 (May 4, 2019). "Plasminogen Isoform 1 Precursor [*Homo sapiens*]," 4 pages.
Schott, D. et al. (Dec. 3, 1998). "Therapy With a Purified Plasminogen Concentrate in an Infant With Ligneous Conjunctivitis and Homozygous Plasminogen Deficiency," The New England Journal of Medicine 339(23):1679-1686.
Siconolfi, L.B. et al. (Jun. 15, 2001). "Mice Lacking tPA, uPA, or Plasminogen Genes Showed Delayed Functional Recovery after Sciatic Nerve Crush," J Neurosci, 21(12):4348-4355.
Sima, J. et al. (Apr. 23, 2004, e-pub. Mar. 23, 2004). "The Effect of Angiostatin on Vascular Leakage and VEGF Expression in Rat Retina," FEBS Letters 564(1-2):19-23.
Wang, Q. (Sep. 2005). "Rest and Protection of Pancreatic Islet Beta-Cell," Chinese Nursing Research 19 (9A):1706-1708. * English Abstract.
Zhang, S.X. et al. (Jan. 4, 2006). "Therapeutic Potential of Angiostatin in Diabetic Nephropathy," J. Am. Soc. Nephrol. 17:475-486, 12 pages.
Zhou, H. et al. (Aug. 2011). "Treatment of 62 Cases of Type 2 Diabetes With Plasmin," 30(Suppl):35-36, 3 pages. English Abstract.
Zou, T. et al. (Jan. 2006). "Exogenous Tissue Plasminogen Activator Enhances Peripheral Nerve Regeneration and Functional Recovery After Injury in Mice," J. Neuropathol. Exp. Neurol. 65(1):78-86.

* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: nucleotide sequence coding for the natural
      human plasminogen (Glu-PLG or Glu-plasminogen) without the signal
      peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa aatttccaag     540
accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact ttgtgacatc     720
ccccgctgca acacctcc accatcttct ggtcccacct accagtgtct gaagggaaca     780
ggtgaaaact atcgcgggaa tgtggctgtt accgtgtccg ggcacacctg tcagcactgg     840
agtgcacaga cccctcacac acataacagg acaccagaaa acttcccctg caaaaatttg     900
gatgaaaact actgccgcaa tcctgacgga aaaaggcccc catggtgcca tacaaccaac     960
agccaagtgc ggtgggagta ctgtaagata ccgtcctgtg actcctcccc agtatccacg    1020
gaacaattgg ctcccacagc accacctgag ctaacccctg tggtccagga ctgctaccat    1080
ggtgatggac agagctaccg aggcacatcc tccaccacca caggaaa gaagtgtcag    1140 tcttggtcat ctatgacacc acaccggcac cagaagaccc cagaaaacta cccaaatgct    1200
ggcctgacaa tgaactactg caggaatcca gatgccgata aggcccctg gtgttttacc    1260
```

```
acagacccca gcgtcaggtg ggagtactgc aacctgaaaa aatgctcagg aacagaagcg    1320
agtgttgtag cacctccgcc tgttgtcctg cttccagatg tagagactcc ttccgaagaa    1380
gactgtatgt ttgggaatgg gaaaggatac cgaggcaaga gggcgaccac tgttactggg    1440
acgccatgcc aggactgggc tgcccaggag ccccatagac acagcatttt cactccagag    1500
acaaatccac gggcgggtct ggaaaaaaat tactgccgta accctgatgg tgatgtaggt    1560
ggtccctggt gctacacgac aaatccaaga aaactttacg actactgtga tgtccctcag    1620
tgtgcggccc cttcatttga ttgtgggaag cctcaagtgg agccgaagaa atgtcctgga    1680
agggttgtag gggggtgtgt ggcccaccca cattcctggc cctggcaagt cagtcttaga    1740
acaaggtttg gaatgcactt ctgtggaggc accttgatat ccccagagtg ggtgttgact    1800
gctgcccact gcttggagaa gtccccaagg ccttcatcct acaaggtcat cctgggtgca    1860
caccaagaag tgaatctcga accgcatgtt caggaaatag aagtgtctag gctgttcttg    1920
gagcccacac gaaaagatat tgccttgcta aagctaagca gtcctgccgt catcactgac    1980
aaagtaatcc cagcttgtct gccatcccca aattatgtgg tcgctgaccg gaccgaatgt    2040
ttcatcactg gctggggaga aacccaaggt acttttggag ctggccttct caaggaagcc    2100
cagctccctg tgattgagaa taaagtgtgc aatcgctatg agtttctgaa tggaagagtc    2160
caatccaccg aactctgtgc tgggcatttg gccggaggca ctgacagttg ccagggtgac    2220
agtggaggtc ctctggtttg cttcgagaag gacaaataca ttttacaagg agtcacttct    2280
tggggtcttg gctgtgcacg ccccaataag cctggtgtct atgttcgtgt ttcaaggttt    2340
gttacttgga ttgagggagt gatgagaaat aattaa                              2376
```

<210> SEQ ID NO 2
<211> LENGTH: 791
<212> TYPE: PRT
<213> ORGANISM: Artificial Sequence
<220> FEATURE:
<223> OTHER INFORMATION: amino acid sequence of the natural human
      plasminogen (Glu-PLG or Glu-plasminogen) without the signal
      peptide

<400> SEQUENCE: 2

Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Asn Tyr Asp Gly
            165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
            195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
    370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
    435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
    515                 520                 525

Pro Arg Lys Leu Tyr Asp Tyr Cys Asp Val Pro Gln Cys Ala Ala Pro
    530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

| | | | | | | | | | | | |
|---|---|---|---|---|---|---|---|---|---|---|---|
|Val|Ser|Leu|Arg|Thr|Arg|Phe|Gly|Met|His|Phe|Cys|Gly|Gly|Thr|Leu|
| | | |580| | | |585| | | |590|

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
        610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
            645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
                675                 680                 685

Gln Gly Thr Phe Gly Ala Gly Leu Leu Lys Glu Ala Gln Leu Pro Val
            690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
770                 775                 780

Glu Gly Val Met Arg Asn Asn
785                 790

<210> SEQ ID NO 3
<211> LENGTH: 2433
<212> TYPE: DNA
<213> ORGANISM: Artificial Sequence
<220> FEATURE:
<223> OTHER INFORMATION: nucleotide sequence coding for the natural
      plasminogen (from swiss prot) with the signal peptide

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag aagtatagaa gaatgtgcag caaaatgtga ggaggacgaa gaattcacc     180 tgcagggcat tccaatatca cagtaaagag caacaatgtg tgataatggc tgaaaacagg     240
aagtcctcca taatcattag gatgagagat gtagttttat ttgaaaagaa agtgtatctc     300
tcagagtgca agactgggaa tggaaagaac tacagaggga cgatgtccaa acaaaaaat     360 ggcatcacct gtcaaaaatg gagttccact ctcccccaca gacctagatt ctcacctgct     420
acacacccct cagagggact ggaggagaac tactgcagga atccagacaa cgatccgcag     480
gggccctggt gctatactac tgatccagaa aagagatatg actactgcga cattcttgag     540
tgtgaagagg aatgtatgca ttgcagtgga aaaactatg acggcaaaat ttccaagacc     600
atgtctggac tggaatgcca ggcctgggac tctcagagcc acacgctca tggatacatt     660 ccttccaaat ttccaaacaa gaacctgaag aagaattact gtcgtaaccc cgataggga     720 ctgcggcctt ggtgtttcac caccgacccc aacaagcgct gggaactttg tgacatcccc     780

-continued

| | |
|---|---|
| cgctgcacaa cacctccacc atcttctggt cccacctacc agtgtctgaa gggaacaggt | 840 |
| gaaaactatc gcgggaatgt ggctgttacc gtgtccgggc acacctgtca gcactggagt | 900 |
| gcacagaccc ctcacacaca taacaggaca ccagaaaact tcccctgcaa aaatttggat | 960 |
| gaaaactact gccgcaatcc tgacggaaaa agggccccat ggtgccatac aaccaacagc | 1020 |
| caagtgcggt gggagtactg taagataccg tcctgtgact cctcccagt atccacggaa | 1080 |
| caattggctc ccacagcacc acctgagcta accctgtgg tccaggactg ctaccatggt | 1140 |
| gatggacaga gctaccgagg cacatcctcc accaccacca caggaaagaa gtgtcagtct | 1200 |
| tggtcatcta tgacaccaca ccggcaccag aagaccccag aaaactaccc aaatgctggc | 1260 |
| ctgacaatga actactgcag gaatccagat gccgataaag gccctggtg ttttaccaca | 1320 |
| gaccccagcg tcaggtggga gtactgcaac ctgaaaaaat gctcaggaac agaagcgagt | 1380 |
| gttgtagcac ctccgcctgt tgtcctgctt ccagatgtag agactccttc cgaagaagac | 1440 |
| tgtatgtttg ggaatgggaa aggataccga ggcaagaggg cgaccactgt tactgggacg | 1500 |
| ccatgccagg actgggctgc ccaggagccc catagacaca gcattttcac tccagagaca | 1560 |
| aatccacggg cgggtctgga aaaaaattac tgccgtaacc ctgatggtga tgtaggtggt | 1620 |
| ccctggtgct acacgacaaa tccaagaaaa ctttacgact actgtgatgt ccctcagtgt | 1680 |
| gcggccccctt catttgattg tgggaagcct caagtggagc cgaagaaatg tcctggaagg | 1740 |
| gttgtagggg gtgtgtggc ccacccacat tcctggccct ggcaagtcag tcttagaaca | 1800 |
| aggtttggaa tgcacttctg tggaggcacc ttgatatccc cagagtgggt gttgactgct | 1860 |
| gcccactgct tggagaagtc cccaaggcct tcatcctaca aggtcatcct gggtgcacac | 1920 |
| caagaagtga atctcgaacc gcatgttcag gaaatagaag tgtctaggct gttcttggag | 1980 |
| cccacacgaa aagatattgc cttgctaaag ctaagcagtc ctgccgtcat cactgacaaa | 2040 |
| gtaatcccag cttgtctgcc atccccaaat tatgtggtcg ctgaccggac cgaatgtttc | 2100 |
| atcactggct ggggagaaac ccaaggtact tttggagctg gccttctcaa ggaagcccag | 2160 |
| ctccctgtga ttgagaataa agtgtgcaat cgctatgagt ttctgaatgg aagagtccaa | 2220 |
| tccaccgaac tctgtgctgg gcatttggcc ggaggcactg acagttgcca gggtgacagt | 2280 |
| ggaggtcctc tggtttgctt cgagaaggac aaatacattt tacaaggagt cacttcttgg | 2340 |
| ggtcttggct gtgcacgcc caataagcct ggtgtctatg ttcgtgtttc aaggtttgtt | 2400 |
| acttggattg agggagtgat gagaaataat taa | 2433 |

<210> SEQ ID NO 4
<211> LENGTH: 810
<212> TYPE: PRT
<213> ORGANISM: Artificial Sequence
<220> FEATURE:
<223> OTHER INFORMATION: amino acid sequence coding for the natural
      plasminogen (from swiss prot) with the signal peptide

<400> SEQUENCE: 4

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

-continued

```
Gln Tyr His Ser Lys Glu Gln Gln Cys Val Ile Met Ala Glu Asn Arg
 65                  70                  75                  80

Lys Ser Ser Ile Ile Ile Arg Met Arg Asp Val Val Leu Phe Glu Lys
                 85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
```

| | | 485 | | | | 490 | | | | 495 | | |
|---|---|---|---|---|---|---|---|---|---|---|---|---|
Val Thr Gly Thr Pro Cys Gln Asp Trp Ala Ala Gln Glu Pro His Arg
                500                 505                 510

His Ser Ile Phe Thr Pro Glu Thr Asn Pro Arg Ala Gly Leu Glu Lys
                515                 520                 525

Asn Tyr Cys Arg Asn Pro Asp Gly Asp Val Gly Pro Trp Cys Tyr
                530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
                580                 585                 590

Pro Trp Gln Val Ser Leu Arg Thr Arg Phe Gly Met His Phe Cys Gly
                595                 600                 605

Gly Thr Leu Ile Ser Pro Glu Trp Val Leu Thr Ala Ala His Cys Leu
                610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
                675                 680                 685

Pro Asn Tyr Val Val Ala Asp Arg Thr Glu Cys Phe Ile Thr Gly Trp
                690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
                755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 2145
<212> TYPE: DNA
<213> ORGANISM: Artificial Sequence
<220> FEATURE:
<223> OTHER INFORMATION: nucleotide sequence coding for LYS77-PLG or
      Lys-plasminogen

<400> SEQUENCE: 5
aaagtgtatc tctcagagtg caagactggg aatggaaaga actacagagg gacgatgtcc     60
aaaacaaaaa atgcatcac ctgtcaaaaa tggagttcca cttctcccca cagacctaga    120
ttctcacctg ctacacaccc ctcagaggga ctggaggaga actactgcag gaatccagac    180

-continued

| | |
|---|---|
| aacgatccgc agggccctg gtgctatact actgatccag aaaagagata tgactactgc | 240 |
| gacattcttg agtgtgaaga ggaatgtatg cattgcagtg gagaaaacta tgacggcaaa | 300 |
| atttccaaga ccatgtctgg actggaatgc caggcctggg actctcagag cccacacgct | 360 |
| catggataca ttccttccaa atttccaaac aagaacctga agaagaatta ctgtcgtaac | 420 |
| cccgataggg agctgcggcc ttggtgtttc accaccgacc caacaagcg ctgggaactt | 480 |
| tgtgacatcc cccgctgcac aacacctcca ccatcttctg gtcccaccta ccagtgtctg | 540 |
| aagggaacag gtgaaaacta tcgcgggaat gtggctgtta ccgtgtccgg cacacctgt | 600 |
| cagcactgga gtgcacagac ccctcacaca cataacagga caccagaaaa cttcccctgc | 660 |
| aaaaatttgg atgaaaacta ctgccgcaat cctgacggaa aagggcccc atggtgccat | 720 |
| acaaccaaca gccaagtgcg gtgggagtac tgtaagatac cgtcctgtga ctcctcccca | 780 |
| gtatccacgg aacaattggc tcccacagca ccacctgagc taaccctgt ggtccaggac | 840 |
| tgctaccatg gtgatggaca gagctaccga ggcacatcct ccaccaccac acaggaaag | 900 |
| aagtgtcagt cttggtcatc tatgacacca caccggcacc agaagacccc agaaaactac | 960 |
| ccaaatgctg gcctgacaat gaactactgc aggaatccag atgccgataa aggcccctgg | 1020 |
| tgttttacca cagaccccag cgtcaggtgg agtactgca acctgaaaaa atgctcagga | 1080 |
| acagaagcga gtgttgtagc acctccgcct gttgtcctgc ttccagatgt agagactcct | 1140 |
| tccgaagaag actgtatgtt tgggaatggg aaaggatacc gaggcaagag ggcgaccact | 1200 |
| gttactggga cgccatgcca ggactgggct gcccaggagc ccatagaca cagcattttc | 1260 |
| actccagaga caaatccacg ggcgggtctg gaaaaaaatt actgccgtaa ccctgatggt | 1320 |
| gatgtaggtg gtccctggtg ctacacgaca aatccaagaa aactttacga ctactgtgat | 1380 |
| gtccctcagt gtgcggcccc ttcatttgat tgtgggaagc tcaagtgga gccgaagaaa | 1440 |
| tgtcctggaa gggttgtagg ggggtgtgtg gcccaccac attcctggcc ctggcaagtc | 1500 |
| agtcttagaa caaggtttgg aatgcacttc tgtggaggca ccttgatatc cccagagtgg | 1560 |
| gtgttgactg ctgcccactg cttggagaag tccccaaggc cttcatccta caaggtcatc | 1620 |
| ctgggtgcac accaagaagt gaatctcgaa ccgcatgttc aggaaataga agtgtctagg | 1680 |
| ctgttcttgg agcccacacg aaaagatatt gccttgctaa agctaagcag tcctgccgtc | 1740 |
| atcactgaca aagtaatccc agcttgtctg ccatccccaa attatgtggt cgctgaccgg | 1800 |
| accgaatgtt tcatcactgg ctggggagaa acccaaggta cttttggagc tggccttctc | 1860 |
| aaggaagccc agtccctgt gattgagaat aaagtgtgca atcgctatga gtttctgaat | 1920 |
| ggaagagtcc aatccaccga actctgtgct gggcatttgg ccggaggcac tgacagttgc | 1980 |
| cagggtgaca gtgaggtcc tctggtttgc ttcgagaagg acaaatacat tttacaagga | 2040 |
| gtcacttctt ggggtcttgg ctgtgcacgc cccaataagc ctggtgtcta tgttcgtgtt | 2100 |
| tcaaggtttg ttacttggat tgagggagtg atgagaaata attaa | 2145 |

<210> SEQ ID NO 6
<211> LENGTH: 714
<212> TYPE: PRT
<213> ORGANISM: Artificial Sequence
<220> FEATURE:
<223> OTHER INFORMATION: amino acid sequence of LYS77-PLG or Lys-plasminogen

<400> SEQUENCE: 6

Lys Val Tyr Leu Ser Glu Cys Lys Thr Gly Asn Gly Lys Asn Tyr Arg
1               5                   10                  15

```
Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415

His Ser Ile Phe Thr Pro Glu Thr Asn Pro Arg Ala Gly Leu Glu Lys
            420                 425                 430
```

```
Asn Tyr Cys Arg Asn Pro Asp Gly Asp Val Gly Gly Pro Trp Cys Tyr
            435                 440                 445

Thr Thr Asn Pro Arg Lys Leu Tyr Asp Tyr Cys Asp Val Pro Gln Cys
450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
        515                 520                 525

Glu Lys Ser Pro Arg Pro Ser Ser Tyr Lys Val Ile Leu Gly Ala His
    530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
        595                 600                 605

Gly Glu Thr Gln Gly Thr Phe Gly Ala Gly Leu Leu Lys Glu Ala Gln
    610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
        675                 680                 685

Ala Arg Pro Asn Lys Pro Gly Val Tyr Val Arg Val Ser Arg Phe Val
    690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial Sequence
<220> FEATURE:
<223> OTHER INFORMATION: nucleotide sequence coding for delta-plg or
      delta-plasminogen

<400> SEQUENCE: 7
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag gacgatgtc caaaacaaaa     300 aatggcatca cctgtcaaaa atggagttcc acttctcccc acagacctag attctcacct     360
gctacacacc cctcagaggg actggaggag aactactgca ggaatccaga caacgatccg     420
```

```
cagggcccct  ggtgctatac  tactgatcca  gaaaagagat  atgactactg  cgacattctt    480
gagtgtgaag  aggcggcccc  ttcatttgat  tgtgggaagc  ctcaagtgga  gccgaagaaa    540
tgtcctggaa  gggttgtagg  ggggtgtgtg  gcccaccac   attcctggcc  ctggcaagtc    600
agtcttagaa  caaggtttgg  aatgcacttc  tgtggaggca  ccttgatatc  ccagagtgg    660 gtgttgactg  ctgcccactg  cttggagaag  tccccaaggc  cttcatccta  caaggtcatc    720
ctgggtgcac  accaagaagt  gaatctcgaa  ccgcatgttc  aggaaataga  agtgtctagg    780
ctgttcttgg  agcccacacg  aaaagatatt  gccttgctaa  agctaagcag  tcctgccgtc    840
atcactgaca  agtaatccc   agcttgtctg  ccatccccaa  attatgtggt  cgctgaccgg    900
accgaatgtt  tcatcactgg  ctggggagaa  acccaaggta  cttttggagc  tggccttctc    960
aaggaagccc  agctccctgt  gattgagaat  aaagtgtgca  atcgctatga  gtttctgaat   1020
ggaagagtcc  aatccaccga  actctgtgct  gggcatttgg  ccggaggcac  tgacagttgc   1080
cagggtgaca  gtggaggtcc  tctggtttgc  ttcgagaagg  acaaatacat  tttacaagga   1140
gtcacttctt  ggggtcttgg  ctgtgcacgc  cccaataagc  ctggtgtcta  tgttcgtgtt   1200
tcaaggtttg  ttacttggat  tgagggagtg  atgagaaata  attaa                    1245
```

<210> SEQ ID NO 8
<211> LENGTH: 414
<212> TYPE: PRT
<213> ORGANISM: Artificial Sequence
<220> FEATURE:
<223> OTHER INFORMATION: amino acid sequence of delta-plg or delta-
      plasminogen

<400> SEQUENCE: 8

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
```

| | | | | 210 | | | 215 | | | 220 | |
|---|---|---|---|---|---|---|---|---|---|---|---|
Ala His Cys Leu Glu Lys Ser Pro Arg Pro Ser Ser Tyr Lys Val Ile
225 230 235 240

Leu Gly Ala His Gln Glu Val Asn Leu Glu Pro His Val Gln Glu Ile
245 250 255

Glu Val Ser Arg Leu Phe Leu Glu Pro Thr Arg Lys Asp Ile Ala Leu
260 265 270

Leu Lys Leu Ser Ser Pro Ala Val Ile Thr Asp Lys Val Ile Pro Ala
275 280 285

Cys Leu Pro Ser Pro Asn Tyr Val Val Ala Asp Arg Thr Glu Cys Phe
290 295 300

Ile Thr Gly Trp Gly Glu Thr Gln Gly Thr Phe Gly Ala Gly Leu Leu
305 310 315 320

Lys Glu Ala Gln Leu Pro Val Ile Glu Asn Lys Val Cys Asn Arg Tyr
325 330 335

Glu Phe Leu Asn Gly Arg Val Gln Ser Thr Glu Leu Cys Ala Gly His
340 345 350

Leu Ala Gly Gly Thr Asp Ser Cys Gln Gly Asp Ser Gly Gly Pro Leu
355 360 365

Val Cys Phe Glu Lys Asp Lys Tyr Ile Leu Gln Gly Val Thr Ser Trp
370 375 380

Gly Leu Gly Cys Ala Arg Pro Asn Lys Pro Gly Val Tyr Val Arg Val
385 390 395 400

Ser Arg Phe Val Thr Trp Ile Glu Gly Val Met Arg Asn Asn
405 410

<210> SEQ ID NO 9
<211> LENGTH: 1104
<212> TYPE: DNA
<213> ORGANISM: Artificial Sequence
<220> FEATURE:
<223> OTHER INFORMATION: nucleotide sequence coding for Mini-plg or
      mini-plasminogen

<400> SEQUENCE: 9
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aggataccg aggcaagagg gcgaccactg ttactgggac gccatgccag      180
gactgggctg cccaggagcc ccatagacac agcattttca ctccagagac aaatccacgg     240
gcgggtctgg aaaaaaatta ctgccgtaac cctgatggtg atgtaggtgg tcctggtgc      300 tacacgacaa atccaagaaa actttacgac tactgtgatg tccctcagtg tgcggcccct    360
tcatttgatt gtgggaagcc tcaagtggag ccgaagaaat gtcctggaag ggttgtaggg     420
gggtgtgtgg cccacccaca ttcctggccc tggcaagtca gtcttagaac aaggtttgga     480
atgcacttct gtggaggcac cttgatatcc ccagagtggg tgttgactgc tgcccactgc    540
ttggagaagt ccccaaggcc ttcatcctac aaggtcatcc tgggtgcaca ccaagaagtg    600
aatctcgaac cgcatgttca ggaaatagaa gtgtctaggc tgttcttgga gcccacacga    660
aaagatattg ccttgctaaa gctaagcagt cctgccgtca tcactgacaa agtaatccca    720
gcttgtctgc catccccaaa ttatgtggtc gctgaccgga ccgaatgttt catcactggc    780
tggggagaaa cccaaggtac ttttggagct ggccttctca aggaagccca gctccctgtg    840
attgagaata agtgtgcaa tcgctatgag tttctgaatg gaagagtcca atccaccgaa     900

```
ctctgtgctg ggcatttggc cggaggcact gacagttgcc agggtgacag tggaggtcct    960
ctggtttgct tcgagaagga caaatacatt ttacaaggag tcacttcttg gggtcttggc   1020
tgtgcacgcc ccaataagcc tggtgtctat gttcgtgttt caaggtttgt tacttggatt   1080
gagggagtga tgagaaataa ttaa                                          1104
```

<210> SEQ ID NO 10
<211> LENGTH: 367
<212> TYPE: PRT
<213> ORGANISM: Artificial Sequence
<220> FEATURE:
<223> OTHER INFORMATION: amino acid sequence of Mini-plg or mini-plasminogen

<400> SEQUENCE: 10

```
Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
        35                  40                  45

Lys Arg Ala Thr Thr Val Thr Gly Thr Pro Cys Gln Asp Trp Ala Ala
50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205

Ile Glu Val Ser Arg Leu Phe Leu Glu Pro Thr Arg Lys Asp Ile Ala
210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
        290                 295                 300

His Leu Ala Gly Gly Thr Asp Ser Cys Gln Gly Asp Ser Gly Gly Pro
305                 310                 315                 320
```

```
Leu Val Cys Phe Glu Lys Asp Lys Tyr Ile Leu Gln Gly Val Thr Ser
            325                 330                 335

Trp Gly Leu Gly Cys Ala Arg Pro Asn Lys Pro Gly Val Tyr Val Arg
        340                 345                 350

Val Ser Arg Phe Val Thr Trp Ile Glu Gly Val Met Arg Asn Asn
    355                 360                 365

<210> SEQ ID NO 11
<211> LENGTH: 750
<212> TYPE: DNA
<213> ORGANISM: Artificial Sequence
<220> FEATURE:
<223> OTHER INFORMATION: nucleotide sequence coding for Micro-plg or
      micro-plasminogen

<400> SEQUENCE: 11
gccccttcat ttgattgtgg gaagcctcaa gtggagccga agaaatgtcc tggaagggtt      60 gtagggggt gtgtggccca cccacattcc tggccctggc aagtcagtct tagaacaagg     120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg agaaacccca aggtactttt ggagctggcc ttctcaagga gcccagctc    480 cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750

<210> SEQ ID NO 12
<211> LENGTH: 249
<212> TYPE: PRT
<213> ORGANISM: Artificial Sequence
<220> FEATURE:
<223> OTHER INFORMATION: amino acid sequence coding for Micro-plg or
      micro-plasminogen

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
```

```
                115                 120                 125
Asn Tyr Val Val Ala Asp Arg Thr Glu Cys Phe Ile Thr Gly Trp Gly
            130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Pro Leu Val Cys Phe Glu Lys
        195                 200                 205

Asp Lys Tyr Ile Leu Gln Gly Val Thr Ser Trp Gly Leu Gly Cys Ala
210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 13
<211> LENGTH: 684
<212> TYPE: DNA
<213> ORGANISM: Artificial Sequence
<220> FEATURE:
<223> OTHER INFORMATION: nucleotide sequence coding for the serine
      protease domain

<400> SEQUENCE: 13

```
gttgtagggg ggtgtgtggc ccacccacat tcctggccct ggcaagtcag tcttagaaca    60
aggtttggaa tgcacttctg tggaggcacc ttgatatccc cagagtgggt gttgactgct   120
gcccactgct tggagaagtc cccaaggcct tcatcctaca aggtcatcct gggtgcacac   180
caagaagtga atctcgaacc gcatgttcag gaaatagaag tgtctaggct gttcttggag   240
cccacacgaa aagatattgc cttgctaaag ctaagcagtc ctgccgtcat cactgacaaa   300
gtaatcccag cttgtctgcc atccccaaat tatgtggtcg ctgaccggac cgaatgtttc   360
atcactggct ggggagaaac ccaaggtact tttggagctg gccttctcaa ggaagcccag   420
ctccctgtga ttgagaataa agtgtgcaat cgctatgagt ttctgaatgg aagagtccaa   480
tccaccgaac tctgtgctgg catttggcc ggaggcactg acagttgcca gggtgacagt   540
ggaggtcctc tggtttgctt cgagaaggac aaatacattt tacaaggagt cacttcttgg   600
ggtcttggct gtgcacgccc caataagcct ggtgtctatg ttcgtgtttc aaggtttgtt   660
acttggattg agggagtgat gaga                                          684
```

<210> SEQ ID NO 14
<211> LENGTH: 228
<212> TYPE: PRT
<213> ORGANISM: Artificial Sequence
<220> FEATURE:
<223> OTHER INFORMATION: amino acid sequence coding for the serine
      protease domain

<400> SEQUENCE: 14

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
```

```
                35                  40                  45
Arg Pro Ser Ser Tyr Lys Val Ile Leu Gly Ala His Gln Glu Val Asn
        50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
                100                 105                 110

Val Ala Asp Arg Thr Glu Cys Phe Ile Thr Gly Trp Gly Glu Thr Gln
                115                 120                 125

Gly Thr Phe Gly Ala Gly Leu Leu Lys Glu Ala Gln Leu Pro Val Ile
                130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
                180                 185                 190

Ile Leu Gln Gly Val Thr Ser Trp Gly Leu Gly Cys Ala Arg Pro Asn
                195                 200                 205

Lys Pro Gly Val Tyr Val Arg Val Ser Arg Phe Val Thr Trp Ile Glu
        210                 215                 220

Gly Val Met Arg
225
```

METHOD FOR PREVENTING OR TREATING DIABETIC RETINOPATHY

CROSS REFERENCE TO RELATED APPLICATIONS

This application is a National Phase application under 35 U.S.C. § 371 of International Application No. PCT/CN2016/110452, filed Dec. 16, 2016, which claims priority to International Application No. PCT/CN2015/097946, filed Dec. 18, 2015, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000300SEQLIST.TXT, date recorded: Jun. 11, 2018, size: 8 KB).

TECHNICAL FIELD

The present invention relates to the use of plasminogen in the inhibition of injuries of tissue cells of internal organs and the blood vessels thereof, and injuries of nerves and retinal tissue cells caused by diabetes mellitus, and also relates to the use of plasminogen in the prevention or treatment of retinopathy caused by diabetes mellitus, thereby providing a brand new prevention and/or treatment strategy for preventing and/or treating different types of retinopathy caused by diabetes mellitus.

BACKGROUND ART

Diabetes mellitus is a group of endocrine and metabolic syndromes of disordered metabolisms of carbohydrates, proteins, fats, water and electrolytes in the body caused by reduced insulin secretion or defects in insulin function resulting from combined action of a variety of genetic and environmental factors. It is characterized by chronic increase in blood glucose level, and leads to chronic complications of the eyes, kidneys, liver and other organs after a long illness. Diabetes mellitus itself and its complications seriously endanger human health, and the treatment of diabetes mellitus and its complications has become a major global public health problem.

Diabetic retinopathy is the most common diabetic eye disease, and often leads to diminution of vision or blindness. According to statistics, 50% of diabetics will have this disease in about 10 years of the disease course, and the figure will reach up to 80% in 15 years or more. The more severe the condition of diabetes mellitus is, the older the patient is, the higher the incidence of the disease is.

Plasmin is a key component of the plasminogen activation system (PA system). It is a broad-spectrum protease that can hydrolyze several components of the extracellular matrix (ECM), including fibrin, gelatin, fibronectin, laminin, and proteoglycan [1]. In addition, plasmin can activate some pro-matrix metalloproteinases (pro-MMPs) to form active matrix metalloproteinases (MMPs). Therefore, plasmin is considered to be an important upstream regulator of extracellular proteolysis [2,3]. Plasmin is formed by proteolysis of plasminogen by two physiological PAs: tissue plasminogen activator (tPA) or urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. There are uPA-specific cell surface receptors (uPARs) that have direct hydrolytic activity on certain cell surfaces [4,5].

Plasminogen (plg) is a single-stranded glycoprotein with a molecular weight of about 92 kDa [6,7]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids [8,9]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease [10]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered 38 kDa of plasminogen is a fragment comprising kringles 1-4, is a potent inhibitor of angiogenesis. This fragment is named as angiostatin and can be produced by the proteolysis of plasminogen via several proteases.

The main substrate of plasmin is fibrin, and the dissolution of fibrin is the key to prevent pathological thrombosis [11]. Plasmin also has substrate specificity for several components of ECM, including laminin, fibronectin, proteoglycan and gelatin, indicating that plasmin also plays an important role in ECM remodeling [7,12,13]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis [14]. In addition, plasmin has the ability to activate certain potential forms of growth factors [15-17]. In vitro, plasmin can also hydrolyze components of the complement system and release chemotactic complement fragments.

The existing treatment method mainly includes basic treatment, namely, auxiliary treatment which is carried out for eye disorders through regular eye examination on the basis of the blood glucose control. We have surprisingly found with spontaneous diabetic mice as research objects that plasminogen and/or plasmin has a good therapeutic effect and high safety in the inhibition of tissue injuries of internal organs, blood vessels, nerves, and the retina and in the prevention or treatment of diabetic retinopathy. Therefore, plasminogen may become a new strategy for treating diabetes mellitus complications including retinopathy.

BRIEF DESCRIPTION OF THE INVENTION

In one aspect, the invention relates to a method for repairing injuries of tissue cells of internal organs caused by diabetes mellitus in a subject, comprising administering plasminogen or plasmin to the subject. In one aspect, the present invention also relates to the use of plasminogen or plasmin for repairing injuries of tissue cells of internal organs caused by diabetes mellitus in a subject, comprising administering plasminogen or plasmin to the subject. In one embodiment, the internal organs include liver, heart, and kidneys. Meanwhile, the invention also relates to a method for repairing injuries of nerves and retinal tissues caused by diabetes mellitus in a subject, and the use of plasminogen or plasmin for repairing injuries of nerves and retinal tissues caused by diabetes mellitus in a subject, comprising administering plasminogen or plasmin to the subject.

The present invention also relates to a method for preventing and/or treating retinopathy caused by diabetes mellitus in a subject, and the use of plasminogen or plasmin for preventing and/or treating retinopathy caused by diabetes mellitus in a subject, comprising administering plasminogen or plasmin to the subject.

In one embodiment, the retinopathy includes retinal neovascularization, retinal inflammation, retinal atrophy, retinal cell apoptosis, retinal tissue structural injury, and retinal vascular injury caused by diabetes mellitus. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has plasminogen activity. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, including topical, intravenous, intramuscular, subcutaneous, inhalation, intraspinal or rectal administration, local injection administration, and/or local administration on cornea by a gene gun, subconjunctival injection, intracameral injection, administration via an eye drop on the cornea, injection into the anterior chamber via the temporal edge, intrastromal injection, corneal application in combination with electric pulses, intracorneal injection, subretinal injection, intravitreal injection and intraocular injection administration. In one embodiment, the plasminogen can be administered in combination with one or more other drugs, including anti-diabetic drugs, drugs against cardiovascular and cerebrovascular diseases, anti-thrombotic drugs, anti-hypertensive drugs, antilipemic drugs, anti-infective drugs as well as other conventional drugs for preventing and/or treating concomitant diseases.

In one embodiment, the subject is a mammal, preferably human.

In one embodiment, the retinopathy caused by diabetes mellitus is caused by diabetes mellitus-induced microangiopathy.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

The above-mentioned plasminogen can be administered alone or in combination with other drugs, and can also be administered in combination with therapies other than drug prevention and/or treatment for retinopathy, such as laser treatment.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In one aspect, the present invention relates to the use of plasminogen or plasmin in the manufacture of a medicament, article, or kit for repairing injuries of internal organs and blood vessel tissues thereof caused by diabetes mellitus in a subject. In one embodiment, the internal organs include liver, heart, and kidneys. Meanwhile, the present invention relates to the use of plasminogen or plasmin in manufacture of a medicament, article, or kit for repairing injuries of nerves and retinal tissues caused by diabetes mellitus in a subject. The present invention also relates to the use of plasminogen or plasmin in the manufacture of a medicament, article, or kit for preventing and/or treating retinopathy caused by diabetes mellitus in a subject. In one embodiment, the retinopathy includes retinal neovascularization, retinal inflammation, retinal atrophy, retinal cell apoptosis, retinal tissue structural injury, and retinal vascular apoptosis.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has plasminogen activity. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, including topical, intravenous, intramuscular, subcutaneous, inhalation, intraspinal or rectal administration, local injection administration, and/or local administration on cornea by a gene gun, subconjunctival injection, intracameral injection, administration via an eye drop on the cornea, injection into the anterior chamber via the temporal edge, intrastromal injection, corneal application in combination with electric pulses, intracorneal injection, subretinal injection, intravitreal injection and intraocular injection administration. In one embodiment, the plasminogen can be administered in combination with one or more other drugs, including anti-diabetic drugs, drugs against cardiovascular and cerebrovascular diseases, anti-thrombotic drugs, anti-hypertensive drugs, antilipemic drugs, anti-infective drugs as well as other conventional drugs for preventing and/or treating concomitant diseases.

In one embodiment, the subject is a mammal, preferably human.

In one embodiment, the retinopathy caused by diabetes mellitus is caused by diabetes mellitus-induced microangiopathy.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

The above-mentioned plasminogen can be administered alone or in combination with other drugs, and can also be administered in combination with therapies other than drug prevention and/or treatment for retinopathy, such as laser treatment.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In another aspect, the present invention relates to plasminogen or plasmin for repairing tissue injuries of internal organs and the blood vessels thereof caused by diabetes mellitus in a subject, and a pharmaceutical composition which comprises plasminogen or plasmin and is useful in repairing tissue injuries of internal organs and the blood vessels thereof caused by diabetes mellitus in a subject, or an article or kit containing the composition. In one embodiment, the internal organs include liver, heart, and kidneys.

Meanwhile, the present invention relates to plasminogen or plasmin for repairing injuries of nerves and retinal tissues caused by diabetes mellitus in a subject, and a pharmaceutical composition which comprises plasminogen or plasmin and is useful in repairing injuries of nerves and retinal tissues caused by diabetes mellitus in a subject, or an article or kit containing the composition. The present invention also relates to plasminogen or plasmin for preventing and/or treating retinopathy caused by diabetes mellitus in a subject, and a pharmaceutical composition which comprises plasminogen or plasmin and is useful in the prevention and/or treatment of retinopathy caused by diabetes mellitus in a subject, and an article or a kit containing the composition. In one embodiment, the retinopathy includes retinal neovascularization, retinal inflammation, retinal atrophy, retinal cell apoptosis, retinal tissue structural injury, and retinal vascular apoptosis.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has plasminogen activity. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, including topical, intravenous, intramuscular, subcutaneous, inhalation, intraspinal or rectal administration, local injection administration, and/or local administration on cornea by a gene gun, subconjunctival injection, intracameral injection, administration via an eye drop on the cornea, injection into the anterior chamber via the temporal edge, intrastromal injection, corneal application in combination with electric pulses, intracorneal injection, subretinal injection, intravitreal injection and intraocular injection administration. In one embodiment, the plasminogen can be administered in combination with one or more other drugs, including anti-diabetic drugs, drugs against cardiovascular and cerebrovascular diseases, anti-thrombotic drugs, anti-hypertensive drugs, antilipemic drugs, anti-infective drugs as well as other conventional drugs for preventing and/or treating concomitant diseases.

In one embodiment, the subject is a mammal, preferably human.

In one embodiment, the retinopathy caused by diabetes mellitus is caused by diabetes mellitus-induced microangiopathy.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

The above-mentioned plasminogen can be administered alone or in combination with other drugs, and can also be administered in combination with therapies other than drug prevention and/or treatment for retinopathy, such as laser treatment.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In one embodiment, the article or kit comprises a container containing an effective dosage of plasminogen/plasmin. Preferably, the article or kit further comprises a container containing one or more other drugs. The article or kit may also include instructions for use, which indicate that the plasminogen or plasmin can be used to prevent and/or treat injuries of internal organs and blood vessel tissues thereof, injuries of nerves and retinal tissues, or the retinal disorder caused by diabetes mellitus, and it may further be stated that the plasminogen or plasmin may be administered before, simultaneously with, and/or after the administration of other drugs or therapies.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In one aspect, the present invention relates to the use of plasminogen in preparing a medicament, article, or kit for preventing and/or treating diabetic ocular microangiopathy in a subject. The present invention also relates to a new method for preventing and/or treating diabetic ocular microangiopathy in a subject, or the use of plasminogen or plasmin for preventing and/or treating diabetic ocular microangiopathy in a subject, comprising administering plasminogen or plasmin to the subject. In another aspect, the present invention relates to plasminogen or plasmin for preventing and/or treating diabetic ocular microangiopathy in a subject, or a pharmaceutical composition which comprises plasminogen or plasmin and is useful in the prevention and/or treatment of diabetic ocular microangiopathy in a subject, or an article or kit which comprises plasminogen or plasmin and is useful in the prevention and/or treatment of diabetic ocular microangiopathy in a subject.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

The above-mentioned prevention and treatment of diabetic ocular microangiopathy include inhibition of the formation of retinal cell-free capillaries, improvement of retinal atrophy, repair of retinal inflammation, and/or inhibition of apoptosis of retinal cells and vascular cells.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

In one aspect, the present invention relates to the use of plasminogen or plasmin in the manufacture of a medicament, article or kit for preventing and/or treating injury (damage) to body tissues and internal organs caused by diabetes mellitus in a subject. In one embodiment, the injury (damage) to tissues and internal organs includes injury (damage) to the brain, heart, liver, lungs, kidneys, nerves, retina, skin and gastrointestinal tract. In one aspect, the present invention relates to the use of plasminogen in the manufacture of a medicament, article or kit for preventing and/or treating a diabetic complication in a subject. In one embodiment, the diabetic complication is diabetic encephalopathy, diabetic cardiopathy, diabetic hepatopathy, diabetic nephropathy, diabetic pneumonopathy, diabetic neuropathy, diabetic retinopathy or diabetic dermopathy induced by diabetes mellitus.

In one aspect, the present invention relates to a method for manufacturing a medicament, comprising preparing a medicament, article or kit for preventing and/or treating injury (damage) to body tissues and internal organs caused by diabetes mellitus in a subject using plasminogen or plasmin and a pharmaceutically acceptable carrier. In one embodiment, the injury (damage) to tissues and internal organs includes injury (damage) to the brain, heart, liver, lungs, kidneys, nerves, retina, skin and gastrointestinal tract. In one aspect, the present invention relates to a method for manufacturing a medicament, comprising preparing a medicament, article or kit for preventing and/or treating a diabetic complication in a subject using plasminogen or plasmin and a pharmaceutically acceptable carrier. In one embodiment, the diabetic complication is diabetic encephalopathy, diabetic cardiopathy, diabetic hepatopathy, diabetic nephropathy, diabetic pneumonopathy, diabetic neuropathy, diabetic retinopathy or diabetic dermopathy induced by diabetes mellitus.

In one aspect, the present invention relates to plasminogen or plasmin, and a pharmaceutical composition, article or kit comprising the plasminogen or plasmin, which are useful in the prevention and/or treatment of injury (damage) to body tissues and internal organs caused by diabetes mellitus in a subject. In one embodiment, the injury (damage) to tissues and internal organs includes injury (damage) to the brain, heart, liver, kidneys, lungs, nerves, retina, gastrointestinal tract and skin. In one aspect, the present invention relates to plasminogen, and a pharmaceutical composition, article or kit comprising the plasminogen, which are useful in the prevention and/or treatment of a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic retinopathy or diabetic dermopathy induced by diabetes mellitus.

In one aspect, the present invention relates to a method for preventing and/or treating injury (damage) to body tissues and internal organs caused by diabetes mellitus in a subject, comprising administering plasminogen or plasmin or a pharmaceutical composition, article or kit comprising the plasminogen or plasmin to the subject. The present invention also relates to the use of plasminogen or plasmin, or a pharmaceutical composition, article or kit comprising the plasminogen or plasmin for preventing and/or treating injury (damage) to body tissues and internal organs caused by diabetes mellitus in a subject. In one embodiment, the injury (damage) to tissues and internal organs includes injury (damage) to the brain, heart, liver, lungs, kidneys, nerves, retina, gastrointestinal tract and skin. In one aspect, the present invention relates to a method for preventing and/or treating a diabetic complication in a subject, comprising administering plasminogen or plasmin, or a pharmaceutical composition, article or kit comprising the plasminogen or plasmin to the subject. The present invention also includes the use of plasminogen or plasmin, or a pharmaceutical composition, article or kit comprising the plasminogen or plasmin for preventing and/or treating a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic retinopathy or diabetic dermopathy induced by diabetes mellitus.

In one embodiment, the subject has a low level of plasmin or plasminogen. Specifically, the low level is innate, secondary and/or local.

The present invention explicitly encompasses all the combinations of technical features belonging to the embodiments of the present invention, and these combined technical solutions have been explicitly disclosed in the present application, as if the above technical solutions were individually and explicitly disclosed. In addition, the present invention also explicitly encompasses all the subcombinations of the various embodiments and elements thereof, and these subcombinations have been disclosed herein, as if each of such subcombinations was individually and explicitly disclosed herein.

DETAILED DESCRIPTION OF EMBODIMENTS

1. Definition

"Diabetes mellitus" is a series of dysmetabolic syndromes of carbohydrates, proteins, fats, water, electrolytes and the like that are caused by islet hypofunction, insulin resistance and the like resulting from the effects of genetic factors, immune dysfunction, microbial infections and toxins thereof, free radical toxins, mental factors and other various pathogenic factors on the body, and is mainly characterized by hyperglycemia clinically.

"Diabetic complications" are damages to or dysfunctions of other organs or tissues of the body caused by poor blood glucose control during diabetes mellitus, including damages to or dysfunctions of the liver, kidneys, heart, retina, nervous system damage and the like. According to statistics of the World Health Organization, there are up to more than 100 diabetic complications, and diabetes mellitus is a disease currently known to have the most complications.

"Diabetic microangiopathy" refers to microangiopathy caused by varying degrees of abnormalities in the microcirculation of various body organs or tissues of diabetics. The process of microangiopathy formation roughly comprises functional changes in microcirculation, endothelial injury, thickening of the basement membrane, increased blood viscosity, aggregation of red blood cells, and adhesion and aggregation of platelets, eventually leading to microthrombosis and/or microvascular occlusion. "Diabetic ocular microangiopathy" refers to ocular microangiopathy caused by diabetes mellitus.

The above-mentioned "diabetic microangiopathy" causes local vascular injury in tissues or organs, poor blood flow, hypoxia of cells, and formation of blood clots, thrombi, and inflammation, and further affects peripheral tissues and organ functions, thereby leading to "diabetic complications"; therefore, the terms "diabetic microangiopathy" and "diabetic complications" mentioned in the technical solutions of the claims of the present invention all cover thrombosis caused by diabetes mellitus.

"Diabetic retinopathy" refers to the diabetes mellitus-induced histological and functional changes of the retina being mainly caused by diabetic microangiopathy. Diabetic retinopathy is the most common diabetic eye disease, and often leads to diminution of vision or blindness. According to statistics, 50% of diabetics will have this disease in about 10 years of the disease course, and the figure will reach up to 80% in 15 years or more. The more severe the condition of diabetes mellitus is, the older the patient is, the higher the incidence of the disease is.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No.4) of the natural human-derived plasminogen containing a signal peptide, is a glycoprotein composed of 810 amino acids, which has a molecular weight of about 92 kD and is synthesized mainly in the liver and capable of circulating in the blood; and the cDNA sequence encoding this amino acid sequence is as shown in SEQ ID No.3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No.1; and the amino acid sequence is as shown in SEQ ID No.2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain [18,19]. The amino acid sequence (SEQ ID No.8) of δ-plasminogen has been reported in the literature [19], and the cDNA sequence encoding this amino acid sequence is as shown in SEQ ID No.7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid) [20]; the amino acid sequence is as shown in SEQ ID No.10; and the cDNA sequence encoding this amino acid sequence is as shown in SEQ ID No.9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid) [21], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A); the amino acid sequence is as shown in SEQ ID No.12; and the cDNA sequence encoding this amino acid sequence is as shown in SEQ ID No.11.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID NO: 14, or an amino acid sequence having an amino acid sequence identity of at least 80%, 90%, 95%, 96%, 97%, 98% or 99% with SEQ ID NO: 14. Therefore, plasminogen of the present invention comprises a protein comprising the plasminogen active fragment and still having plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the PLG in the test plasma is converted into PLM by the action of SK, PLM acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogen derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity and hydrophobicity). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowly method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues), and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

$$\text{fraction } X/Y \times 100$$

wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

2. Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus,* for example, *Bacillus subtilis* and other species of *Enterobacteriaceae* (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (eg, mammalian cells cultured in in vitro cell culture) can also be used to express and produce the protein of the invention (eg, polynucleotides encoding the subject protein). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the plasminogen and the like.

3. Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEEN™, PLURONICS™ or polyethylene glycol (PEG).

The formulations of the invention may also comprise one or more active compounds required for the particular disorder to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58,481), copolymer of L-glutamic acid and γ ethyl-L-glutamic acid (Sidman et al. Biopolymers 22:547(1983)), non-degradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(−)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulfhydryl residues, lyophilizing from acidic solutions, controlling moisture content, using appropriate additives, and developing specific polymer matrix compositions.

4. Administration and Dosage

The pharmaceutical composition of the present invention can be administered in different ways, for example by intravenous, intraperitoneal, subcutaneous, intracranial, intrathecal, intraarterial (e.g., via carotid), intramuscular, intranasal, intraocular, topical or intradermal administration or spinal cord or brain delivery. An aerosol preparation, such as a nasal spray preparation, comprises purified aqueous or other solutions of the active agent along with a preservative and isotonic agent. For intraocular administration, such preparations need to be adjusted to a pH and isotonic state compatible with the ocular conjunctiva.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety of diabetic retinopathy and its related disorders are required to be assessed real-timely and regularly.

5. Treatment Efficacy and Treatment Safety

One embodiment of the present invention relates to the judgment of treatment efficacy and treatment safety after treating a subject with plasminogen/plasmin. The methods for judging the treatment efficacy include, but are not limited to: 1) the correction of a subject's vision: after treating the subject with the plasminogen of the present invention, the vision of the patient is expected to be restored or improved, for example, the patient's vision, stereo vision, contrast sensitivity, dark adaptation, color vision, and visual field are expected to be restored or improved; 2) electrophysiological examinations, including for example electroretinogram, electrooculogram, visual evoked potential, etc.; 3) fundus examinations, including direct and indirect funduscopy, slit lamp examination under three mirrors, fundus fluorescein angiography, OCT, etc.; 4) optic nerve examinations, including examination of the subject's neuropathy, extraocular muscle paralysis, dysadaptation, optic atrophy, etc., for expecting that the function of the optic nerve in the subject will be restored or improved after receiving the plasminogen treatment of the present invention; 5) in the case of refractive error, blood glucose elevation can cause decreased osmotic pressure of aqueous humor, infiltration of the aqueous humor into lens, and change of the refractive power, leading to myopia, while the decreased blood glucose causes increased osmotic pressure of the aqueous humor and extravasated water from the lens, forming the opposing hyperopia; it is expected that after the subject receives the plasminogen treatment of the present invention, the function of the optic nerve will be restored or improved; and 6) intraocular pressure examinations for expecting that the subject's intraocular pressure will return to normal or be improved after treatment with the plasminogen of the present invention, such as between 10 mmHg and 21 mmHg. In addition, the present invention also relates to the monitoring and assessment of adverse drug reactions required to be performed during and after treating a subject with plasminogen.

6. Articles or Kits

One embodiment of the invention relates to an article or kit comprising the plasminogen of the invention useful in the treatment of retinopathy and its related disorders caused by diabetes mellitus. The article preferably includes a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen. The label on or attached to the container indicates that the composition is used to treat retinopathy and its related disorders caused by diabetes mellitus according to the present invention. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to a user of the composition to administer the plasminogen composition and other drugs to treat an accompanying disease to a patient.

EXAMPLES

Figure 1:
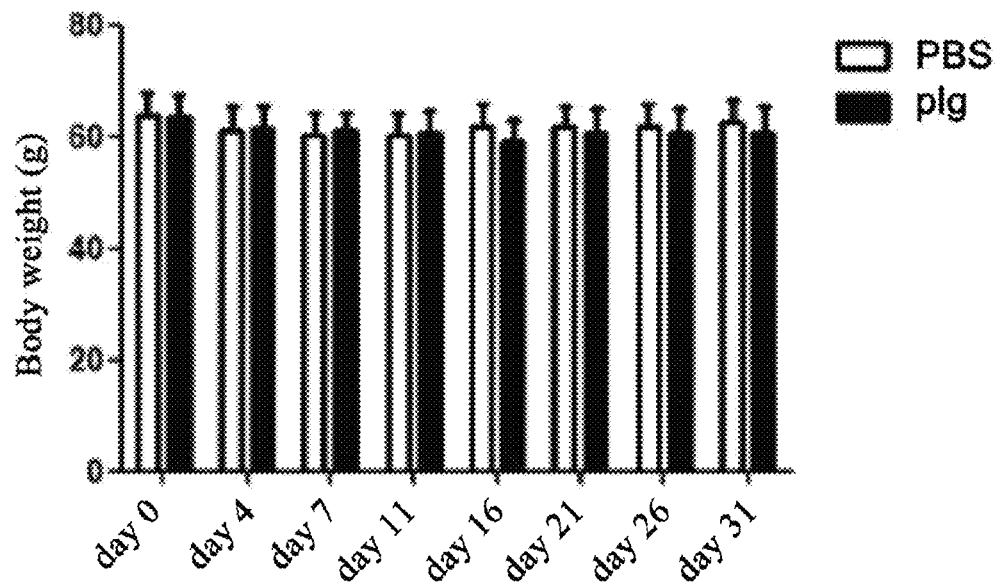
FIG. 1 shows changes in body weight after administration of plasminogen to 24-25-week-old diabetic mice for 31 consecutive days. The result shows that plasminogen has little effect on animal body weight.

1. Experimental Animals:

C57BLKS-derived db/db diabetic mice were used, and C57BLKS-derived db/+heterozygous mice were used as the normal control, which were purchased at Nanjing Biomedical Research Institute. 10-week-old or older mice with blood glucose levels of higher than 15 mM in db/db mice were used for the experiments, and even-aged db/+heterozygous mice with blood glucose levels of lower than 7.8 mM were used for the control group. The animals were fed in an experimental animal use environment that meets the national standard.

2. Experimental Design:

The selected mice were randomly divided into 2 groups: db/db model group (model group) and db/db plasminogen treatment group (treatment group). Retinopathy was developed in the selected db/db mice when they were 24-25 weeks old, thereafter, the mice were injected with plasminogen at a dosage of 2 mg/0.2 mL/mouse/day via the tail vein for 31 days as an experimental cycle. The day starting to administer plasminogen was recorded as the first day of the experiment. Animals in all groups were subjected to relevant tests on the day before the administration of plasminogen and weekly after starting the experiment.

3. Retinal Vessel Preparation and its PAS Staining and Cell-Free Capillary Counting:

Referencing to the reports of literatures [22-24], retinal vessels were prepared. The specific process was as follows: the eyeballs of mice were removed and immediately fixed in 4% paraformaldehyde PBS buffer overnight; the retina were isolated from the eyeballs and washed with water overnight at room temperature, and then digested with 3% trypsin (Invitrogen, Grand Island, N.Y.) for 2-3 h at 37° C.; the tissues were transferred to purified water, and retinal vessels were separated from the surrounding attachment tissues under a dissecting microscope, fixed on a clean glass slide, naturally dried sufficiently, stained in the PAS solution, rinsed with water, and dehydrated, and the slide was sealed. The prepared retinal vessels were observed under a microscope. PAS staining density was analyzed with Image-Pro Plus 6.0 software.

The number of cell-free capillaries in the 4-6 fields of view in the middle of the retina was randomly counted. A capillary with no cell nucleus only having a capillary wall is called a cell-free capillary [25]. Data were represented by the number of cell-free capillaries per 10 $mm^2$.

4 HE Staining of Retinal Paraffin Section:

The eyeballs of mice were removed and fixed in 4% paraformaldehyde PBS buffer for 24-48 hours. The fixed eyeballs were paraffin-embedded after dehydration with alcohol gradient and permeabilization with xylene. Then paraffin sectioning and HE staining were carried out, and retinopathy was observed under a microscope.

5. Immunohistochemical Staining of Retinal VEGF, Bcl-2, F4/80, and Fibrin [22,26]:

The eyeballs were subjected to routine paraffin sectioning, and the sections were dewaxed, rehydrated, and repaired at high temperature for 15 minutes. The sections were incubated with hydrogen peroxide for 15 minutes. The sections were blocked with 10% normal goat serum solution (Vector laboratories, Inc., USA) for 1 hour, incubated with a primary antibody overnight at 4° C., rinsed with TBS, and a secondary antibody was added dropwise. Then the sections were incubated at room temperature for 1 hour and developed. After counterstaining with hematoxylin, gradient dehydration, permeabilization and sealing, the sections were prepared to be observed. Two retinal sections with intact structures were selected for each eyeball. Five fields of view were randomly selected for each section. Image-Pro Plus 6.0 image processing software was used to analyze the average optical density value of the stained regions in each group.

Example 1

Effect of Plasminogen on Body Weight of Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. The mice were weighted on days 0, 4, 7, 11, 16, 21, 26 and 31.

The results showed that there was no significant difference in body weight between mice in the group administered with plasminogen and those in the control group administered with vehicle PBS on days 0, 4, 7, 11, 16, 21, 26 and 31 (FIG. 1), indicating that plasminogen has little effect on animal body weight.

Example 2

Protective Effect of Plasminogen on the Retina of Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the left eyeballs were fixed in 4% paraformaldehyde for 24 hours. The fixed eyeballs were paraffin-embedded after dehydration with alcohol gradient and permeabilization with xylene. The thickness of the tissue sections was 5 μm. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient and observed under a microscope at 400×.

In diabetic retinopathy, retinal atrophy would occur, and the outer plexiform layer (OPL), the outer nuclear layer (ONL), the photoreceptor layer (PL), and the entire retina would become thinner [27]. Therefore, the thickness parameters of the above four items can be used to determine the situation of retinal injury.

Figure 2:
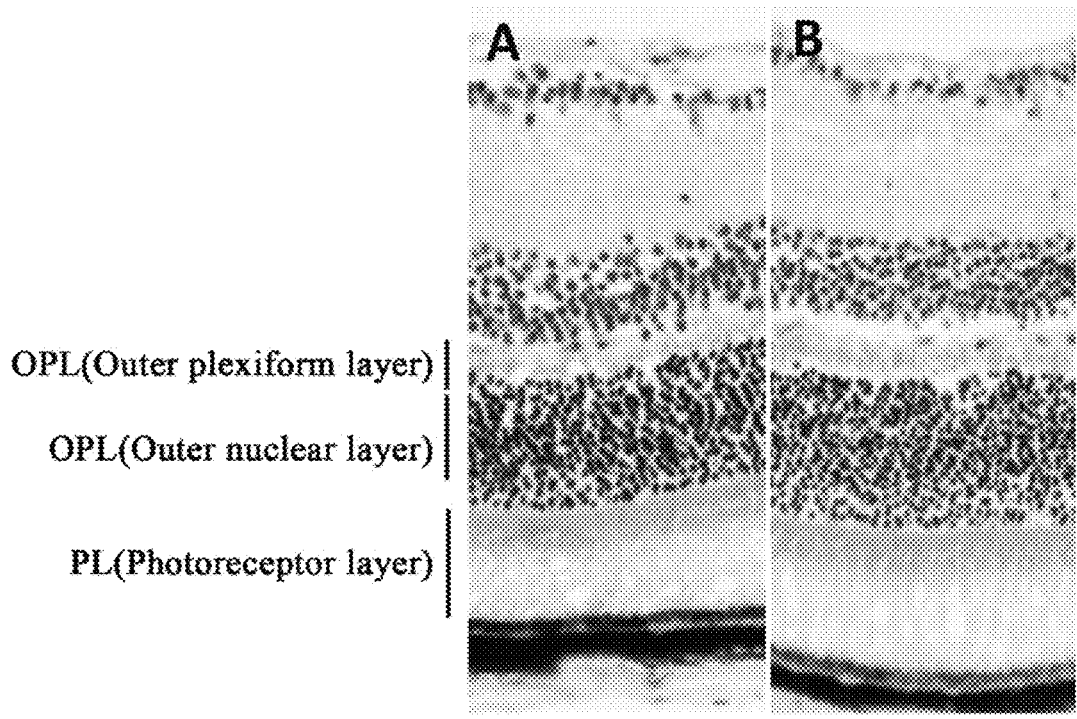
FIG. 2 shows the observed results of HE of the retina after administration of plasminogen to 24-25-week-old diabetic mice for 31 consecutive days.

The result showed that in the retina of mice in the control group administered with vehicle PBS, the structure of each layer was loose, the cells were arranged irregularly, the arrangement of retinal ganglion cells and inner nuclear layer cells were disordered, and the retinal pigment epithelial cells were proliferated (FIG. 2A); compared with the control group administered with vehicle PBS, in the group administered with plasminogen, the cells in each layer in the retina were arranged regularly, and it can be observed that the thickness of the retinal OPL, ONL and PL and the total thickness are thicker (FIG. 2B). This indicated that injection of plasminogen can promote the repair of retinal injury of diabetic mice.

Example 3

Plasminogen Alleviates Retinal Injury of Late Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the left eyeballs were fixed in paraformaldehyde fix solution for 24 hours. The retina was detached from the fixed eyeballs and placed in a 1 mL EP tube containing 3% pancreatin (Solarbio), and shaken for digestion in a shaker at 37° C. for 2-3 h. After the retina was softened and detached, the retina was carefully transferred into an EP tube filled with distilled water and shaken in a shaker at 37° C. for 2-3 h to detach excess tissues from the retina. The retina was gently pipetted, leaving only the blood vessel layer, and then spread on a glass slide and air dried. The retina was stained in periodic acid-Schiff solution (PAS staining), differentiated with 1% hydrochloric acid in alcohol, and returned to blue with ammonia water. The slide was sealed after dehydration with alcohol gradient and permeabilization with xylene, and observed under a microscope at 400×.

Related studies have shown that diabetes mellitus can cause retinopathy, resulting in proliferation of retinal vascular endothelial cells, loss of pericytes and formation of cell-free vessels [28,29].

Figure 3:
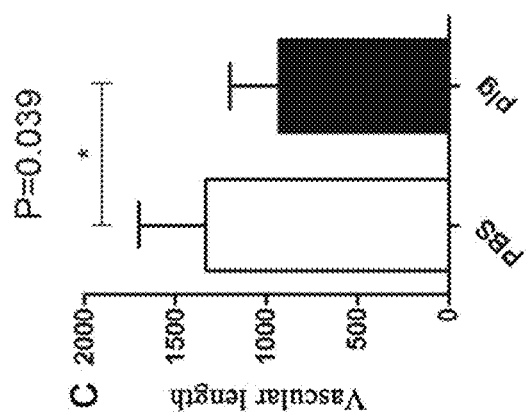
FIG. 3 shows the observed results of PAS staining of the retina after administration of plasminogen to 24-25-week-old diabetic mice for 31 consecutive days.
Figure 3:
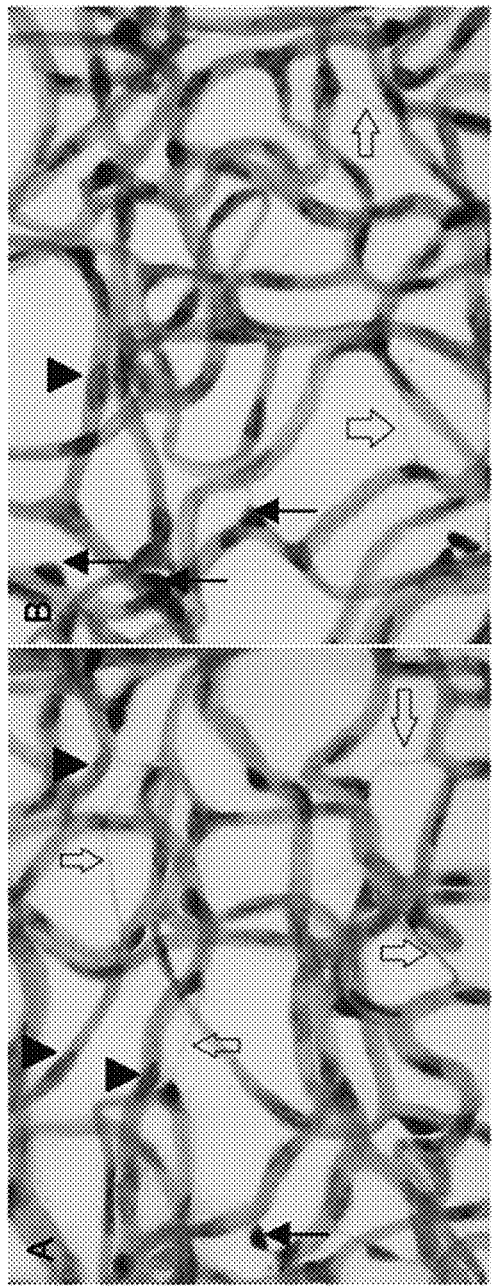

From the experimental results, it can be seen that compared with the plasminogen group (FIG. 3B), the retinal capillary diameters of the db/db mice in the control group administered with vehicle PBS (FIG. 3A) were different, in which the vascular walls were thickened and darkly stained, the vascular endothelial cells (Δ) were proliferated, and the pericytes (↓) were decreased remarkably; however, mice in the group administered with plasminogen had remarkably reduced pathological changes. It was found from quantitative analysis that compared with mice in the control group administered with vehicle PBS, those in the group administered with plasminogen had significantly reduced cell-free vascular length (FIG. 3C), and the statistical analysis results showed a significant difference. This indicated that plasminogen can significantly promote the repair of retinal injury of late diabetic mice.

Example 4

Plasminogen Promotes the Repair of the Retinal Injury in Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. The eyeballs were removed on day 32 and fixed in 4% paraformaldehyde for 24 hours. The fixed eyeballs were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were blocked with 10% normal goat serum solution for 1 hour; and after the time was up, the goat serum solution was discarded, and the tissues were circled with a PAP pen. The sections were incubated with rabbit anti-mouse VEGF antibody (Abcam) at 4° C. overnight and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

VEGF is vascular endothelial growth factor, and its expression is increased in the case of vascular injury in the body [30,31]. Therefore, the expression of VEGF can reflect the condition of vascular injury.

Figure 4:
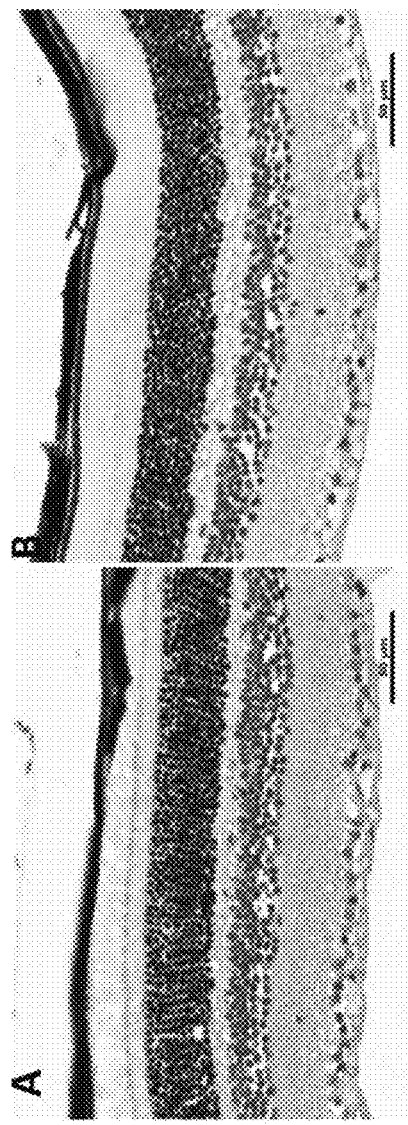
FIG. 4 shows the results of VEGF immunostaining of the retina after administration of plasminogen to 24-25-week-old diabetic mice for 31 consecutive days.

The results showed that the expression of VEGF in each layer of the retina in the control group administered with vehicle PBS (FIG. 4A) was significantly higher than that in the group administered with plasminogen (FIG. 4B), indicating that injection of plasminogen inhibits the expression of retinal VEGF and promotes the repair of the retinal injury in diabetic mice.

Example 5

Plasminogen Promotes Dissolution of Retinal Microthrombi Caused by Diabetes Mellitus Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. 24 hours after the last administration, blood was taken from the removed eyeballs, and the whole blood was left standing to obtain serum for detecting the D-dimer content in the blood.

Figure 5:
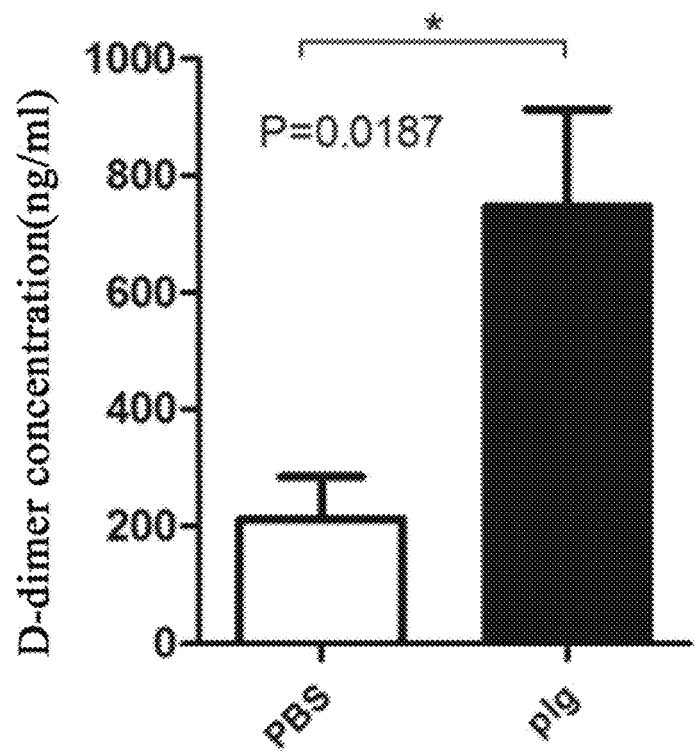
FIG. 5 shows the detection results of D-dimer content in serum after administration of plasminogen to 24-25-week-old diabetic mice for 15 consecutive days.

The results showed that the D-dimer content in the serum of mice was significantly increased after 15 days of administration (FIG. 5), indicating that after administration of plasminogen, retinal microthrombi caused by diabetes mellitus were significantly dissolved.

Example 6

Plasminogen Promotes the Expression of Apoptosis Inhibitory Protein in the Retina of Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. The eyeballs were removed on day 32 and fixed in 4% paraformaldehyde for 24 hours. The fixed eyeballs were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were blocked with 10% normal goat serum solution for 1 hour; then the goat serum solution was discarded, and the tissues were circled with a PAP pen. The sections were incubated with rabbit anti-mouse Bcl-2 antibody (Abcam) at 4° C. overnight and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Figure 6:
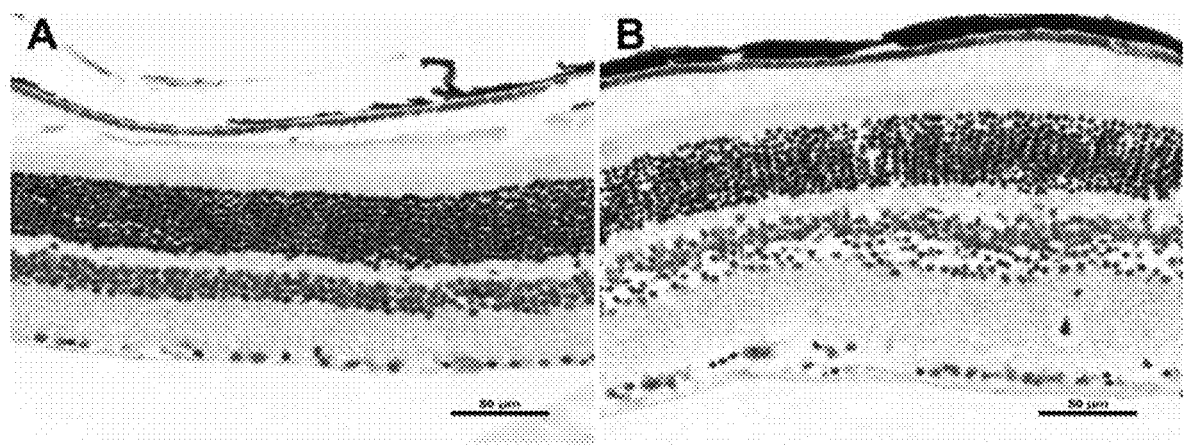
FIG. 6 shows the results of Bcl-2 immunostaining of the retina after administration of plasminogen to 24-25-week-old diabetic mice for 31 consecutive days.

Bcl-2 is an apoptosis inhibitory protein, and its expression will be down-regulated under the action of an apoptosis stimulating factor [32, 33]. The results showed that the expression of Bcl-2 in the retina in the control group administered with vehicle PBS (FIG. 6A) was significantly lower than that in the group administered with plasminogen (FIG. 6B). This indicated that plasminogen can promote the expression of Bcl-2, an apoptosis inhibitory molecule, in the retinal cells of diabetic mice, and thus can inhibit the apoptosis of retinal cells.

Example 7

Plasminogen Promotes the Repair of Myocardial Injury in Late Diabetes Mellitus

Twenty-eight male db/db mice aged 24-25 weeks were randomly divided into two groups, twelve in the control group administered with vehicle PBS and sixteen in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On day 32, blood was taken from the removed eyeballs and centrifuged at 3500 r/min for 15-20 minutes, and the supernatant was used for detection for determining cardiac troponin I concentration.

Figure 7:
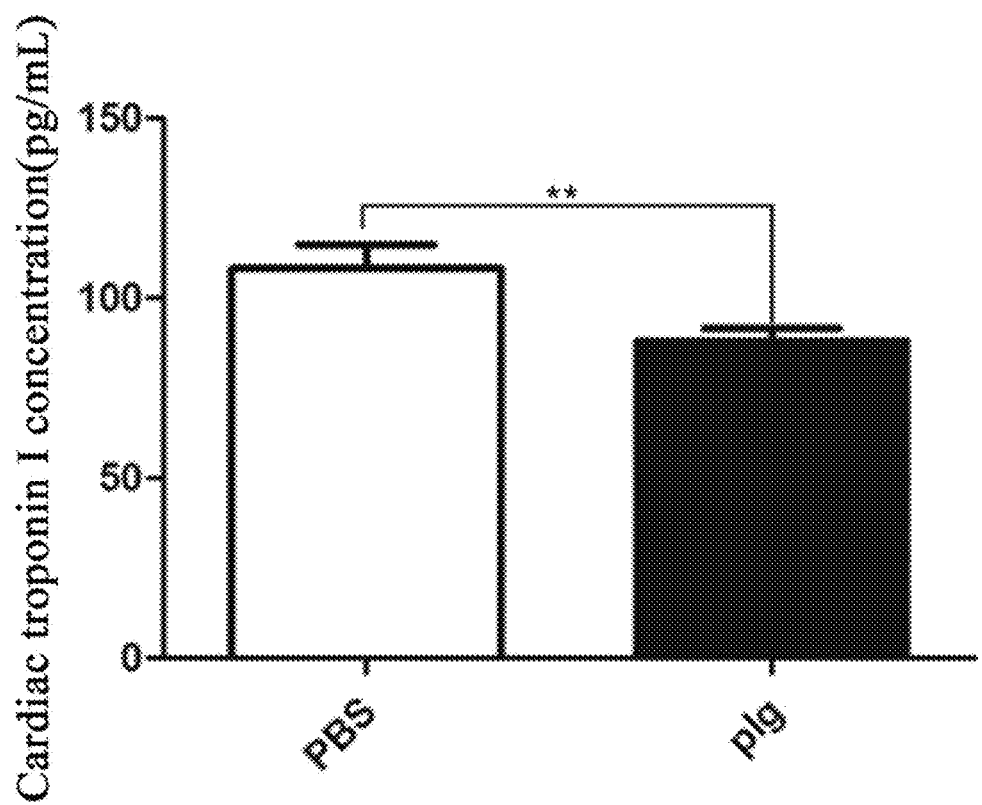
FIG. 7 shows the detection results of cardiac troponin I concentration in serum after administration of plasminogen to 24-25-week-old db/db mice for 31 days.

Cardiac troponin I (CTNI) is an important marker of myocardial injury, and its serum concentration can reflect the extent of myocardial injury [34]. The results showed that the cardiac troponin I concentration in the group administered with plasminogen was significantly lower than that in the control group administered with vehicle PBS, and there was an extremely significant statistical difference (FIG. 7). This indicated that plasminogen can extremely significantly promote the repair of myocardial injury of late diabetic mice.

Example 8

Plasminogen Promotes the Expression of Bcl-2, an Apoptosis Inhibitory Factor, in the Kidneys of Late Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse Bcl-2 antibody (Abcam) at 4° C. overnight and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Figure 8:
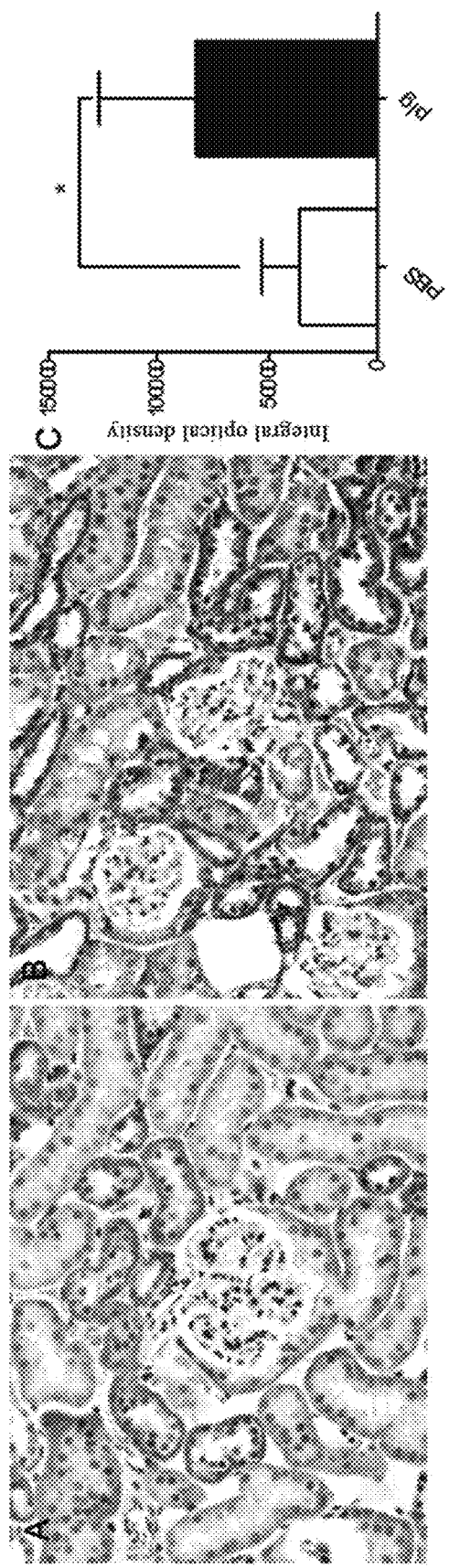
FIG. 8 shows the observed results of Bcl-2 immunostaining of the kidneys after administration of plasminogen to 24-25-week-old db/db mice for 31 consecutive days.

Bcl-2 is an apoptosis inhibitory protein, and its expression will be down-regulated under the action of an apoptosis stimulating factor [32,33]. The Bcl-2 immunohistochemical results showed that the positive expression staining of tubular epithelial cells in mice in the group administered with plasminogen (FIG. 8B) was significantly darker than that of tubular epithelial cells in those in the control group administered with vehicle PBS (FIG. 8A), and the former had a wider range of staining The results of quantitative analysis were consistent with the observations, and there were significant differences (as shown in FIG. 8C). This indicated that plasminogen promotes the expression of Bcl-2, an apoptosis inhibitory molecule, in the kidneys of diabetic mice, and thus can inhibit the apoptosis in the kidney tissues of diabetic mice.

Example 9

Plasminogen Promotes Fibrin Hydrolysis in the Kidneys of Late Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin and deposited at the injury site [35-37]. Therefore, the fibrin level can be used as a sign of the degree of injury.

Figure 9:
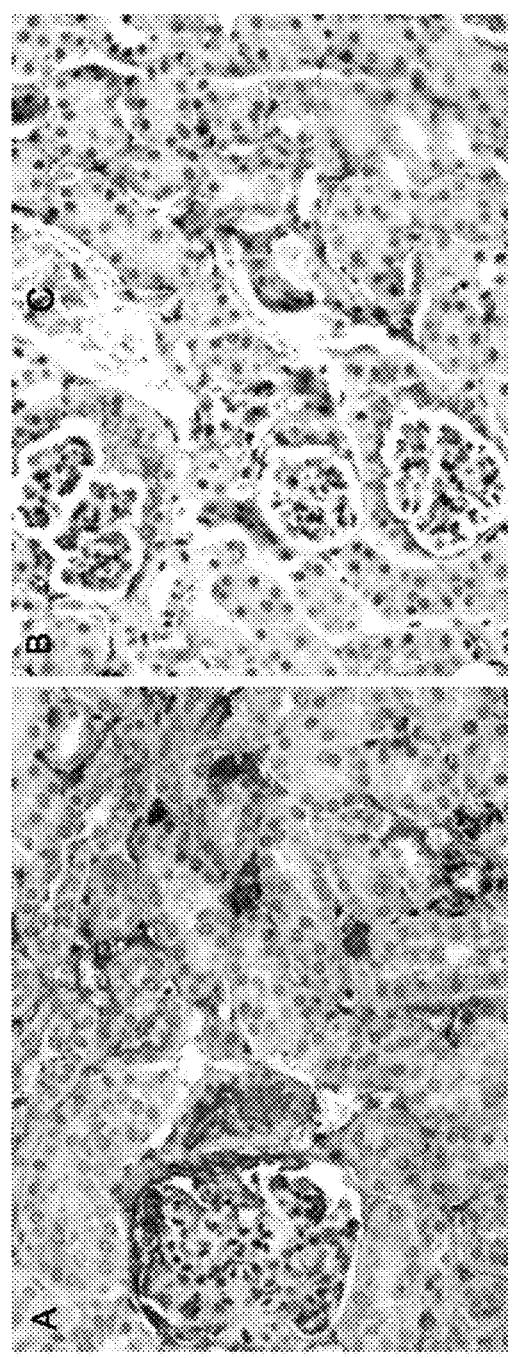
FIG. 9 shows the observed results of fibrin immunostaining of the kidneys after administration of plasminogen to 24-25-week-old db/db mice for 31 consecutive days.

The results showed the fibrinogen-positive staining in the group administered with plasminogen (FIG. 9B) was lighter than that in the control group administered with vehicle PBS (FIG. 9A). This indicated that injection of plasminogen can reduce the deposition of fibrin in diabetic mice, reflecting the repair effect of plasminogen on renal injury in diabetic mice.

Example 10

Plasminogen Promotes the Repair of Liver Injury of Diabetic Mice

Nine male db/db mice aged 25-28 weeks were randomly divided into two groups, three in the control group administered with vehicle PBS and six in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Whole blood was taken from the removed eyeballs 31 days after administration of plasminogen. After the serum was precipitated, it was centrifuged at 3500 r/min for 10 minutes at 4° C., and the supernatant was taken for detection. In this experiment, the content of alanine transaminase (ALT) in serum was detected by Reitman-Frankel colorimetry using an alanine transaminase detection kit (Nanjing Jiancheng Biological Engineering Research Institute, Catalog No. C009-2).

Figure 10:
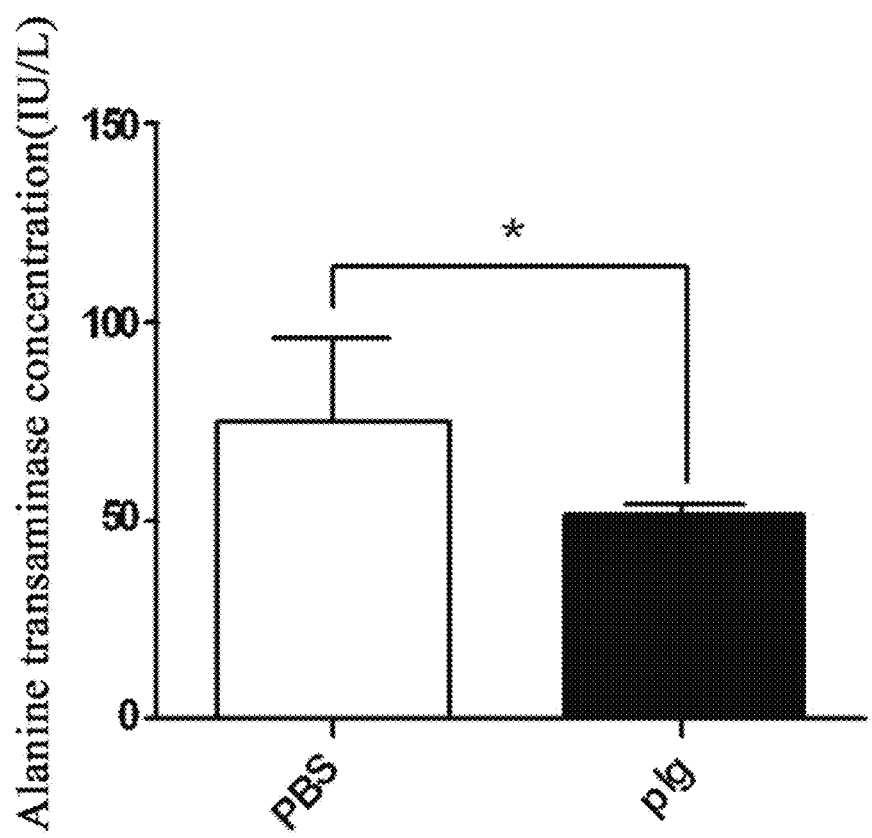
FIG. 10 shows the detection results of ALT in serum after administration of PBS (A) or plasminogen (B) to 24-25-week-old diabetic mice for 31 days.

Alanine transaminase is an important index of liver health status [38,39], and the normal reference value interval of alanine transaminase is 9-50 U/L. The detection results showed that the ALT content in serum of mice in the control group administered with vehicle PBS was significantly higher than the normal physiological index, whereas the content in mice in the group administered with plasminogen had returned to normal levels in the body; and the content in mice in the group administered with plasminogen was significantly lower than that in mice in the control group administered with vehicle PBS, and there was a statistical difference (FIG. 10). This indicated that injection of plasminogen can effectively repair the liver injury in model mice with late diabetic diabetes.

Example 11

Plasminogen Promotes the Inflammation Repair of the Liver Tissues of Late Diabetic Mice Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed 31 days after administration of plasminogen, and liver tissues were fixed in 10% neutral formalin fix solution for 24 hours. The fixed liver tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum (Vector laboratories, Inc., USA) for 1 hour, and after the time was up, the serum was thrown away, and the tissues were circled with a PAP pen. The sections were incubated with a rabbit polyclonal antibody against F4/80 (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Figure 11:
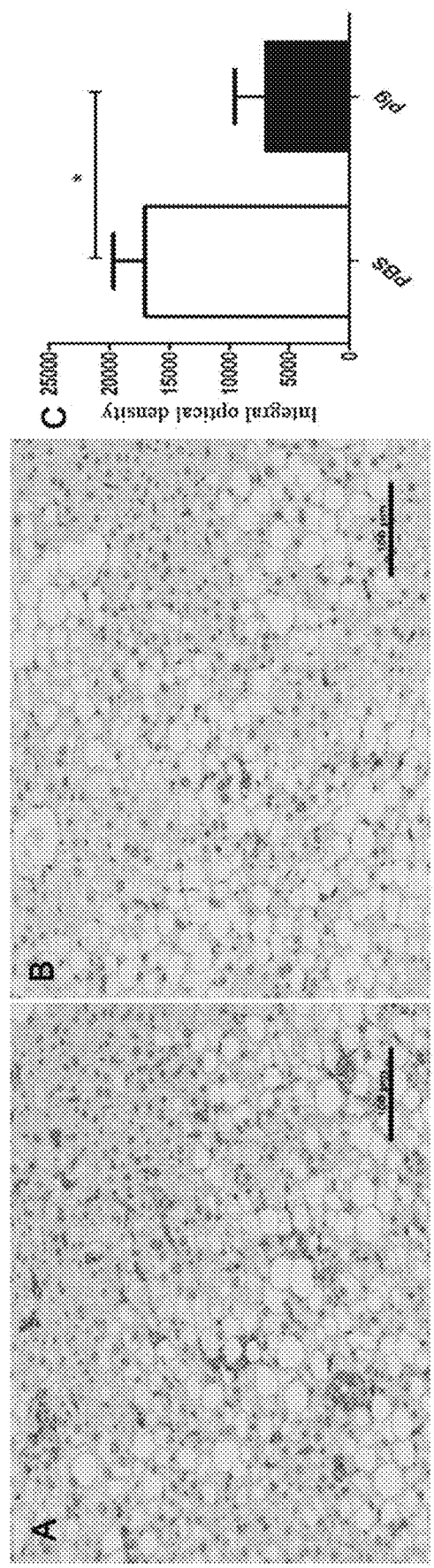
FIG. 11 shows the observed results of fibrin immunostaining of the liver after administration of plasminogen to 24-25-week-old db/db mice for 31 consecutive days.

F4/80 is a macrophage marker that can indicate the extent and stage of an inflammatory response. The results showed that compared with mice in the control group administered with vehicle PBS (FIG. 11A), the F4/80 positive expression was significantly reduced in those in the group administered with plasminogen (FIG. 11B), indicating that inflammation of the liver tissues is reduced after administration of plasminogen. FIG. 11C shows the results of quantitative analysis of F4/80 immunohistochemical positive expression, in which the expression of F4/80 in mice in the group administered with plasminogen was significantly reduced with statistical difference, indicating that plasminogen can significantly reduce the liver inflammation of diabetic mice.

Example 12

Plasminogen Promotes the Repair of the Ability of Late Diabetic Mice with Nerve Injury to Respond to Mechanical Allodynia Ten male db/db mice aged 24-25 weeks were randomly divided into two groups, five in the control group administered with vehicle PBS and five in the group administered with plasminogen, respectively. The day when the experiment began was recorded on Day 0, the mice were weighed and grouped, and the physiological experiment was initiated. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration of plasminogen, animals were detected for their sensitivity to mechanical injury using Von-Frey filaments (Stoelting, USA). With 2.0 g force as the starting force, the left foot was first detected. If there were 2 paw withdrawals for 5 stimulations, it was positive; and if it was positive, the right foot was then stimulated with a smaller force. If it was negative, the right foot was stimulated with a larger force, the left and right feet were thus alternately stimulated for a total of 6 stimulations at a stimulation interval of 5 minutes, and then the 50% paw withdrawal threshold was calculated according to the method introduced in S. R. Chaplan et. al. (1994) [40].

Figure 12:
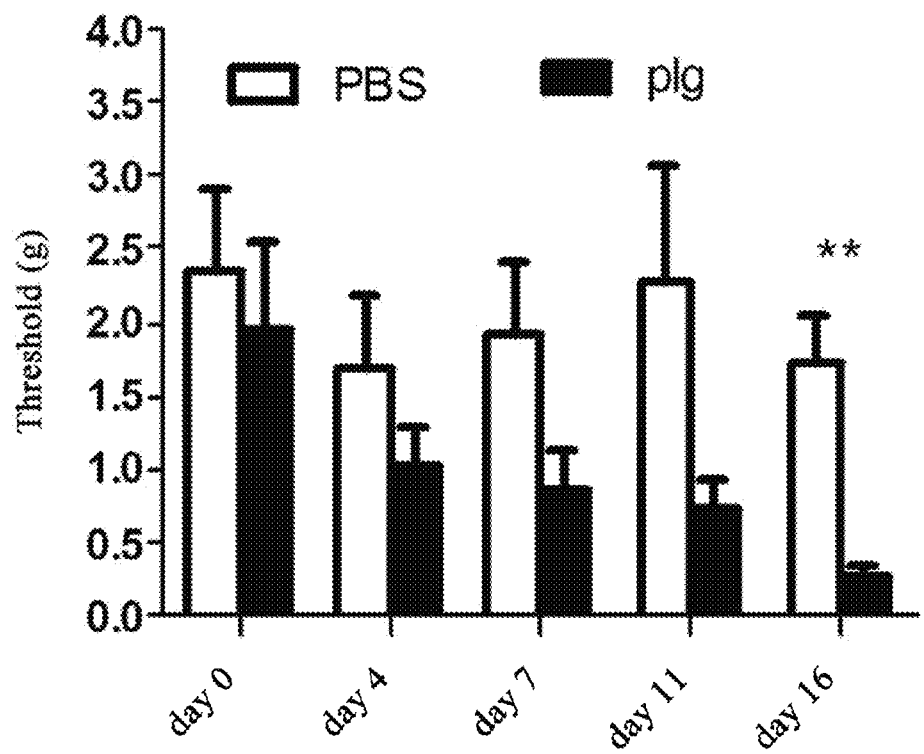
FIG. 12 shows the detection results of the ability to respond to mechanical allodynia on days 0, 4, 7, 11 and 16 after administration of plasminogen to 24-25-week-old db/db mice.

The study found that compared with mice in the control group administered with vehicle PBS, diabetic mice in the group administered with plasminogen showed uniform increase in the response to mechanical allodynia, and an extremely significant difference was found on day 16 compared with mice in the control group administered with vehicle PBS (FIG. 12), indicating that plasminogen repairs the ability of late diabetic mice with nerve injury to respond to mechanical allodynia.

Example 13

Plasminogen Repairs Response of Late Diabetic Mice with Nerve Injury to Cold Stimulation Ten male db/db mice aged 24-25 weeks were randomly divided into two groups, five in the control group administered with vehicle PBS and five in the group administered with plasminogen, respectively. The day when the experiment began was recorded on Day 0, the mice were weighed and grouped, and the physiological experiment was initiated. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration, a drop of acetone was squeezed out with a needleless syringe and the planta of each db/db mouse was slightly touched to cover the entire planta with acetone. Starting from the left foot, the left and right feet were stimulated alternately every 3 minutes for a total of 10 stimulations, and the number of paw withdrawals was counted. Percentage of response=number of paw withdrawals/number of stimulations×100%.

Figure 13:
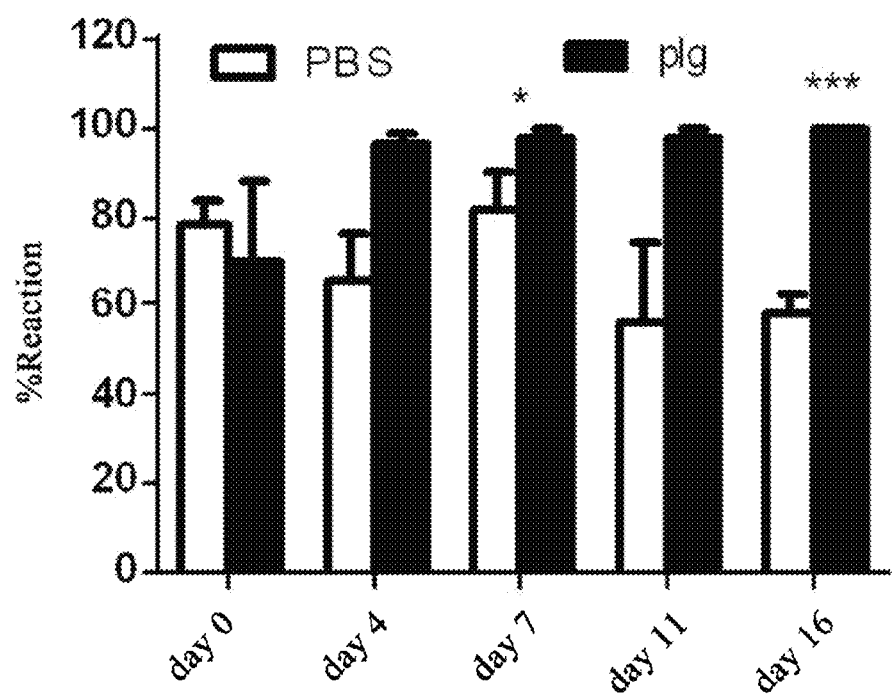
FIG. 13 shows the detection results of the ability to respond to cold stimulation on days 0, 4, 7, 11 and 16 after administration of plasminogen to 24-25-week-old db/db mice.

The experimental results showed that there was no significant difference in the response to acetone stimulation between mice in the group administered with plasminogen and those in the control group administered with vehicle PBS on days 0 and 4; however, a significant difference was observed from day 7, and an extremely significant difference was observed on day 16, and the P value was <0.0001 (FIG. 13), indicating that after 15 days of administration, diabetic mice almost completely restored response to cold stimulation, suggesting that plasminogen extremely significantly repairs the ability of nerves to response to cold stimulation in late diabetes mellitus.

Example 14

Plasminogen Reduces the Fibrin Level in Nerve Tissues of Late Diabetic Mice with Nerve Injury Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 16, and sciatic nerves were fixed in 10% neutral formalin fix solution for 24 hours. The fixed sciatic nerves were paraffin-embedded after dehydration with alcohol gradient and permeabilization with xylene. The thickness of the tissue sections was 5 µm. The sections were dewaxed and rehydrated and washed with water once, and then the tissues were circled with a PAP pen. The sections were incubated with hydrogen peroxide diluted with 3% TBS for 15 minutes, and washed with water three times. The sections were blocked with 10% normal goat serum (Vector laboratories, Inc., USA) for 1 hour, and excess serum was aspirated. The sections were incubated with rabbit anti-mouse fibrin (fibrinogen) antibody (Abcam) for 1 hour at room temperature or overnight at 4° C. and washed with TBS three times. The sections were incubated with a secondary antibody, goat anti-rabbit IgG (HRP) antibody (Abcam), for 1 hour at room temperature and washed with TBS three times. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Fibrinogen is the precursor of fibrin, and in the presence of tissue injury, as a stress response to the body's injury, fibrinogen is hydrolyzed into fibrin. Therefore, fibrin levels can be used as a sign of the degree of injury [35-37]. Fibrin is also the main component of thrombosis after tissue is injured. Therefore, fibrin levels can also be used as a marker of thrombi.

Figure 14:
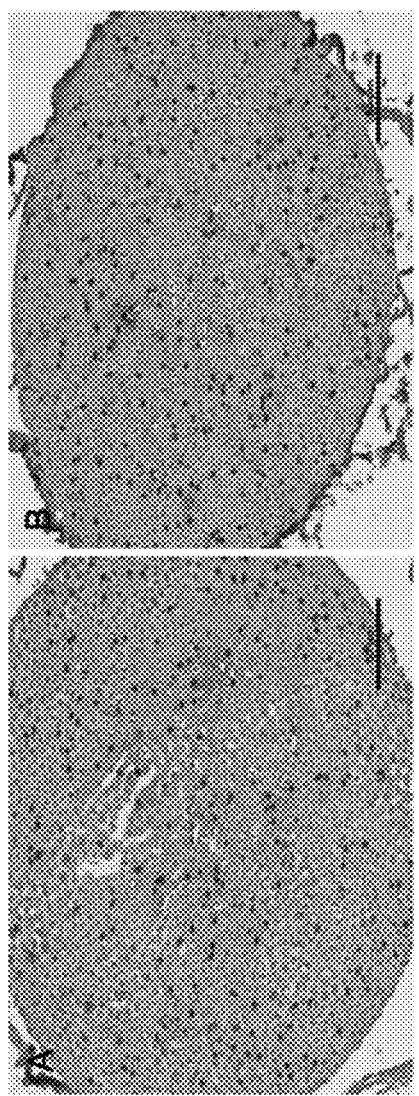
FIG. 14 shows the observed results of fibrin immumohistochemical staining of the sciatic nerve after administration of plasminogen to 24-25-week-old late diabetic mice with nerve injury for 15 consecutive days.

The study found that compared with mice in the control group administered with vehicle PBS (FIG. 14A), those in the group administered with plasminogen (FIG. 14B) had a decreased level of fibrin in the sciatic nerve, indicating that plasminogen has the function of degrading fibrin level and the injury has been repaired to a certain degree, and also indicating that plasminogen can promote the dissolution of thrombi around nerve tissues.

Example 15

Plasminogen Alleviates the Injury of the Kidneys in Late Diabetic Mice

Eight male db/db mice aged 24-25 weeks were randomly divided into two groups, four in the control group administered with vehicle PBS and four in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Detection of physiological indexes was finished on day 32, mice were sacrificed, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were incubated with goat anti-mouse IgM (HRP) antibody (Abcam) for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

IgM antibodies play an important role during the clearance of apoptotic and necrotic cells. The more apoptotic and necrotic cells are, the higher the local IgM antibody level is [41-43]. Therefore, local IgM antibody levels can reflect the injury of tissues and organs.

Figure 15:
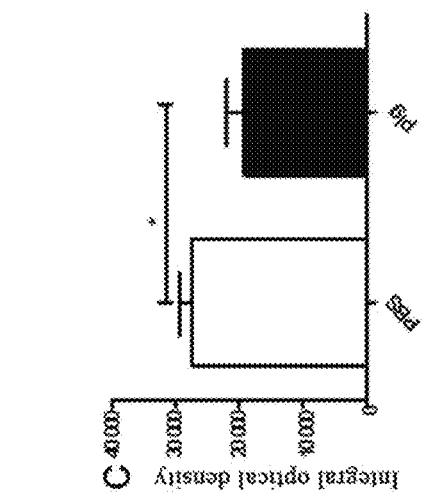
FIG. 15 shows the observed results of IgM immunostaining of the kidneys after administration of plasminogen to 24-25-week-old diabetic mice for 31 days.
Figure 15:
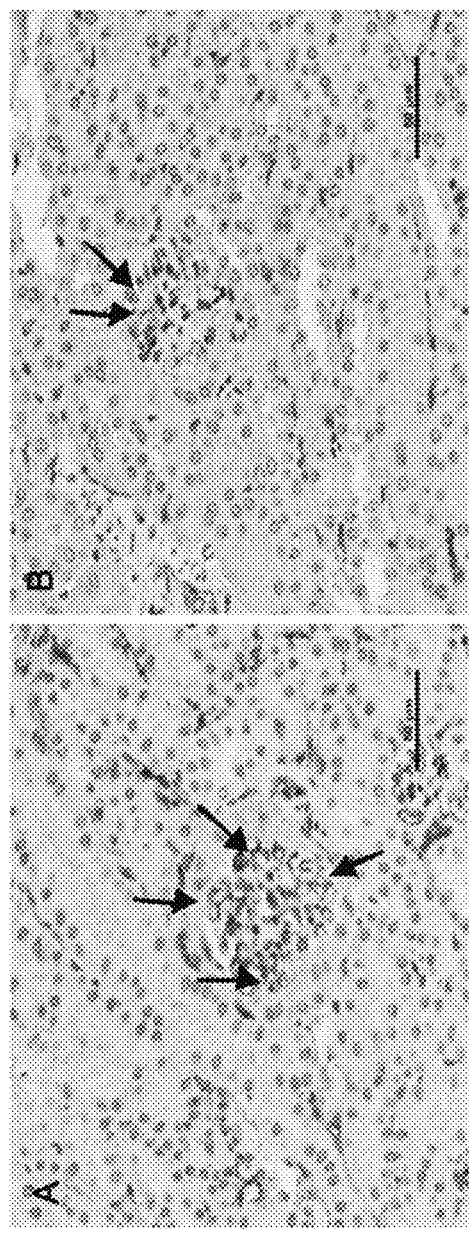

The results showed that the positive staining of glomerular IgMs in mice in the group administered with plasminogen (FIG. 15B) was lighter than that of glomerular IgMs in mice in the control group administered with vehicle PBS (FIG. 15A), the range was also smaller than the control group, and the statistical analysis results were consistent with the observations (FIG. 15C), indicating that the glomerular injury is remarkably improved after injection of plasminogen, reflecting the significant protection and repair functions of plasminogen on the body's injury of diabetic mice.

REFERENCES

[1] Alexander C M and Werb, Z. (1991). Extracellular matrix degradation. In Cell Biology of Extracellular Matrix, Hay ED, ed. (New York: Plenum Press), pp. 255-302

[2] Werb, Z., Mainardi, C. L., Vater, C. A., and Harris, E. D., Jr. (1977). Endogenous activiation of latent collagenase by rheumatoid synovial cells. Evidence for a role of plasminogen activator. N. Engl. J. Med. 296, 1017-1023.

[3] He, C. S., Wilhelm, S. M. , Pentland, A. P., Marmer, B. L., Grant, G. A., Eisen, A. Z., and Goldberg, G. I. (1989). Tissue cooperation in a proteolytic cascade activating human interstitial collagenase. Proc. Natl. Acad. Sci. U.S.A 86, 2632-2636

[4] Stoppelli, M. P., Corti, A., Soffientini, A., Cassani, G, Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U.S.A 82, 4939-4943.

[5] Vassalli, J. D., Baccino, D., and Belin, D. (1985). A cellular binding site for the Mr 55,000 form of the human plasminogen activator, urokinase. J. Cell Biol. 100, 86-92.

[6] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[7] Saksela, O. and Rifkin, D. B. (1988). Cell-associated plasminogen activation: regulation and physiological functions. Annu. Rev. Cell Biol. 4, 93-126

[8] Raum, D., Marcus, D., Alper, C. A., Levey, R., Taylor, P. D., and Starzl, T. E. (1980). Synthesis of human plasminogen by the liver. Science 208, 1036-1037

[9] Wallén P (1980). Biochemistry of plasminogen. In Fibrinolysis, Kline D L and Reddy K K N, eds. (Florida: CRC

[10] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U.S.A 72, 2577-2581.

[11] Collen, D. and Lijnen, H. R. (1991). Basic and clinical aspects of fibrinolysis and thrombolysis. Blood 78, 3114-3124.

[12] Alexander, C. M. and Werb, Z. (1989). Proteinases and extracellular matrix remodeling. Curr. Opin. Cell Biol. 1, 974-982.

[13] Mignatti, P. and Rifkin, D. B. (1993). Biology and biochemistry of proteinases in tumor invasion. Physiol Rev. 73,161-195.

[14] Collen, D. (2001). Ham-Wasserman lecture: role of the plasminogen system in fibrin-homeostasis and tissue remodeling. Hematology. (Am. Soc. Hematol. Educ. Program.) 1-9.

[15] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[16] Andreasen, P. A., Kjoller, L., Christensen, L., and Duffy, M. J. (1997). The urokinase-type plasminogen activator system in cancer metastasis: a review. Int. J. Cancer 72, 1-22.

[17] Rifkin, D. B., Mazzieri, R., Munger, J. S., Noguera, I., and Sung, J. (1999). Proteolytic control of growth factor availability. APMIS 107, 80-85.

[18] Marder V J, Novokhatny V. Direct fibrinolytic agents: biochemical attributes, preclinical foundation and clinical potential[J]. Journal of Thrombosis and Haemostasis, 2010, 8(3): 433-444.

[19] Hunt J A, Petteway Jr S R, Scuderi P, et al. Simplified recombinant plasmin: production and fu-nctional comparison of a novel thrombolytic molecule with plasma-derived plasmin[J]. Thromb Haemost, 2008, 100(3): 413-419.

[20] Sottrup-Jensen L, Claeys H, Zajdel M, et al. The primary structure of human plasminogen: Isolation of two lysine-binding fragments and one "mini"-plasminogen (MW, 38,000) by elastase-catalyzed-specific limited proteolysis[J]. Progress in chemical fibrinolysis and thrombolysis, 1978, 3: 191-209.

[21] Nagai N, Demarsin E, Van Hoef B, et al. Recombinant human microplasmin: production and potential therapeutic properties[J]. Journal of Thrombosis and Haemostasis, 2003, 1(2): 307-313.

[22] Liu, M., et al., NaoXinTong Inhibits the Development of Diabetic Retinopathy in db/db Mice. Evid Based Complement Alternat Med, 2015. 2015: p. 242517.

[23] Liu, M., et al., Administration of Danhong Injection to diabetic db/db mice inhibits the development of diabetic retinopathy and nephropathy. Sci Rep, 2015. 5: p. 11219.

[24] Bell, W. R., W. R. Green, and M. F. Goldberg, Histopathologic and trypsin digestion studies of the retina in incontinentia pigmenti. Ophthalmology, 2008. 115(5): p. 893-7.

[25] Feit-Leichman, R. A., et al., Vascular damage in a mouse model of diabetic retinopathy: relation to neuronal and glial changes. Invest Ophthalmol Vis Sci, 2005. 46(11): p. 4281-7.

[26] 李小璐, 不同病程糖尿病 大鼠视网膜病理改变及其VEGF, PEDF 的动态表达 in 研究 生院 2013, 宁夏医科大学: 银川 . p. 1-59.

[27] Mengyang Liu, Quan Pan, Yuanli Chen et al. NaoXinTong Inhibits the Development of Diabetic Retinopathy in/Mice. Evid Based Complement Alternat Med.2015: 242517.

[28] Cunha-Vaz J, Bernardes R: Nonproliferative retinopathy in diabetes type 2. Initial stages and characterization of phenotypes, Prog Retin Eye Res 2005, 24:355-377.

[29] Roy S, Sato T, Paryani G, Kao R: Downregulation of fibronectin overexpression reduces basement membrane thickening and vascular lesions in retinas of galactose-fed rats. Diabetes 2003, 52: 1229-1234.

[30] Palmer, Biff F.; Clegg, Deborah J. (2014). "Oxygen sensing and metabolic homeostasis". Molecular and Cellular Endocrinology. 397: 51-57.

[31] Cooper, Mark; Dimitria Vranes; Sherif Youssef; Steven A. Stacker; Alison J. Cox; Bishoy Rizkalla; David J. Casley; Leon A. Bach; Darren J. Kelly; Richard E. Gilbert (November 1999). Increased Renal Expression of Vascular Endothelial Growth Factor (VEGF) and Its Receptor VEGFR-2 in Experimental Diabetes". Diabetes. 48 (11): 2229-2239.

[32] Wang L, Chanvorachote P, Toledo D, Stehlik C, Mercer R R, Castranova V, Rojanasakul Y (2008). Peroxide is a key mediator of Bcl-2 down-regulation and apoptosis induction by cisplatinin human lung cancer cells. Mol Pharmacol 73,119-127.

[33] Moungjaroen J, Nimmannit U, Callery P S, Wang L, Azad N, Lipipun V, Chanvorachote P, Rojanasakul Y (2006). Reactive oxygen species mediate caspase activation and apoptosis induced by lipoic acid in human lung epithelial cancer cells through Bcl-2 downregulation. J Pharmacol Exp Ther 319,1062-1069.

[34] R. Langhorn and J. L. Willesen. Cardiac Troponins in Dogs and Cats. J Vet Intern Med 2016;30:36-50.

[35] Dimitrios Davalos Katenna Akassoglou. Fibrinogen as a key regulator of inflammation in disease. Seminars in Immunopathology, 2012. 34(1):43-62.

[36] Valvi D, Mannino D M, Mullerova H, et al. Fibrinogen, chronic obstructive pulmonary disease (COPD) and outcomes in two United States cohorts. Int J Chron Obstruct Pulmon Dis 2012; 7:173-82.

[37] Moungjaroen J, Nimmannit U, Callery P S, Wang L, Azad N, Lipipun V, Chanvorachote P, Rojanasakul Y (2006). Reactive oxygen species mediate caspase activation and apoptosis induced by lipoic acid in human lung epithelial cancer cells through Bcl-2 downregulation. J Pharmacol Exp Ther 319, 1062-1069.

[38] Karmen A, Wroblewski F, Ladue J S (Jan 1955), Transaminase activity in human blood. The Journal of Clinical Investigation. 34 (1): 126-31.

[39] Wang C S, Chang T T, Yao W J, Wang S T, Chou P (Apr 2012), Impact of increasing alanine aminotransferase levels within normal range on incident diabetes. Journal of the Formosan Medical Association=Taiwan Yi Zhi. 111(4): 201-8.

[40] S. R. Chaplan, et al., Quantitative assessment of tactile allodynia in the rat paw, Journal of Neuroscience Methods 53 (1994) 55-63.

[41] Zwart B, Ciurana C, Rensink I, Manoe R, Hack C E, et al. (2004) Complement activation by apoptotic cells occurs predominantly via IgM and is limited to late apoptotic (secondary necrotic) cells. Autoimmunity 37: 95-102.

[42] Zhang M, Takahashi K, Alicot E M, Vorup-Jensen T, Kessler B, et al. (2006) Activation of the lectin pathway by natural IgM in a model of ischemia/reperfusion injury. J Immunol 177: 4727-4734.

[43] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

The invention claimed is:

1. A method for preventing and/or treating retinopathy caused by diabetes mellitus in a subject, comprising administering an effective amount of plasminogen to the subject, wherein the plasminogen is selected from Glu-plasminogen, Lys-plasminogen, mini-plasminogen, micro-plasminogen, δ (delta)-plasminogen or any combination thereof.

2. The method of claim 1, wherein the retinopathy comprises retinal neovascularization, retinal inflammation, retinal atrophy, retinal cell apoptosis, and retinal tissue structural injury caused by diabetes mellitus.

3. The method according to claim 1, wherein the plasminogen has at least 80%, 85%, 90%, 95%, 96%, 97%, 98% or 99% sequence identity with SEQ ID No.2, 6, 8, 10 or 12, and still has the plasminogen activity.

4. The method according to claim 1, wherein the plasminogen is a protein that comprises a plasminogen active fragment and still has the plasminogen activity.

5. The method according to claim 1, wherein the plasminogen is administered systemically or locally.

6. The method according to claim 1, wherein the plasminogen is administered in combination with one or more other drugs.

7. The method of claim 1, wherein the plasminogen is administered by topical, intravenous, intramuscular, subcutaneous, inhalation, intraspinal or rectal administration, local injection administration, and/or local administration on cornea by a gene gun, subconjunctival injection, intracameral injection, administration via an eye drop on the cornea, injection into the anterior chamber via the temporal edge, intrastromal injection, corneal application in combination with electric pulses, intracorneal injection, subretinal injection, intravitreal injection or intraocular injection administration.

8. The method of claim 6, wherein the one or more drugs are selected from the group consisting of anti-diabetic drugs, drugs against cardiovascular and cerebrovascular diseases, anti-thrombotic drugs, anti-hypertensive drugs, antilipemic drugs, anti-infective drugs and other conventional drugs for treating concomitant diseases.

* * * * *